(12) United States Patent
Hertz

(10) Patent No.: US 12,741,070 B2
(45) Date of Patent: Sep. 22, 2026

(54) CONTROL OF FLUID TEMPERATURE IN A DIALYSIS SYSTEM

(71) Applicant: GAMBRO LUNDIA AB, Lund (SE)

(72) Inventor: Thomas Hertz, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 18/866,391

(22) PCT Filed: May 5, 2023

(86) PCT No.: PCT/EP2023/062009
§ 371 (c)(1),
(2) Date: Nov. 15, 2024

(87) PCT Pub. No.: WO2023/222412
PCT Pub. Date: Nov. 23, 2023

(65) Prior Publication Data

US 2025/0319239 A1 Oct. 16, 2025

(30) Foreign Application Priority Data

May 18, 2022 (SE) .................................. 2250594-5

(51) Int. Cl.
*A61M 1/16* (2006.01)
*A61B 18/00* (2006.01)
(Continued)

(52) U.S. Cl.
CPC ............. *A61M 1/1664* (2014.02); *A61F 7/12* (2013.01); *A61M 1/153* (2022.05); *A61M 1/166* (2014.02);
(Continued)

(58) Field of Classification Search
CPC .......... A61M 1/153; A61M 2205/3372; A61M 2205/3626; A61M 2205/3368;
(Continued)

(56) References Cited

U.S. PATENT DOCUMENTS 9,717,834 B2 8/2017 Wilt et al.
2004/0215129 A1 10/2004 Edgson et al.
(Continued)

FOREIGN PATENT DOCUMENTS

EP 3254712 A1 12/2017

OTHER PUBLICATIONS

The Engineering ToolBox (2011), "Mixing Fluids", Available online at: https://www.engineeringtoolbox.com/mixing-fluids-temperature-mass-d_1785.html [Accessed Nov. 15, 2024].
(Continued)

*Primary Examiner* — Atif H Chaudry
(74) *Attorney, Agent, or Firm* — K&L Gates LLP

(57) ABSTRACT

A dialysis system comprises a supply sub-system, a storage sub-system, a treatment sub-system, and a control device. The supply sub-system is arranged to supply a fluid to the storage sub-system and comprises a heating device for heating the fluid. The storage sub-system comprises a non-heated reservoir for receiving the fluid from the supply sub-system. The treatment sub-system is configured to obtain the fluid from the storage sub-system for use in dialysis treatment. The control device operates the supply sub-system to perform a sequence of fluid supply cycles causing a sequence of time-separated boluses of the fluid to be supplied to the reservoir, with each fluid supply cycle being assigned a target temperature and comprising a predefined number of boluses. The supply sub-system is operated to achieve, through the predefined number of boluses, the target temperature of the fluid in the reservoir for the respective fluid supply cycle.

29 Claims, 9 Drawing Sheets

(51) Int. Cl.

| | |
|---|---|
| ***A61F 7/12*** | (2006.01) |
| ***A61M 1/14*** | (2006.01) |
| ***A61M 1/36*** | (2006.01) |
| ***A61M 5/44*** | (2006.01) |
| ***F24H 15/175*** | (2022.01) |
| ***G05D 23/19*** | (2006.01) |

(52) U.S. Cl.
CPC ........ *A61M 1/1662* (2014.02); *A61M 1/3623* (2022.05); *A61M 5/445* (2013.01); *F24H 15/175* (2022.01); *G05D 23/1951* (2013.01); *A61B 2018/00791* (2013.01); *A61F 2007/126* (2013.01); *A61M 2205/3368* (2013.01); *A61M 2205/3372* (2013.01)

(58) Field of Classification Search
CPC ............... A61M 1/1664; A61M 1/1662; A61F 2007/126; A61F 7/12; A61B 2018/00791; F24H 15/175
See application file for complete search history.

(56) References Cited

U.S. PATENT DOCUMENTS

2008/0154197 A1 6/2008 Derrico et al.
2011/0004141 A1* 1/2011 Zhang .................... A61M 1/16 604/6.13
2016/0256582 A1 9/2016 Hertz et al.
2016/0279312 A1 9/2016 Kassab et al.
2019/0160216 A1* 5/2019 Pouchoulin ......... A61M 1/1658
2022/0249751 A1* 8/2022 Kammerzell ....... A61M 1/3609

OTHER PUBLICATIONS

International Search Report for International Patent Application No. PCT/EP2023/062009, mailed Aug. 23, 2023. 3 pages.
Written Opinion of the International Searching Authority (EPO) for International Patent Application No. PCT/EP2023/062009, mailed Aug. 23, 2023. 5 pages.

* cited by examiner

FIC. 4C

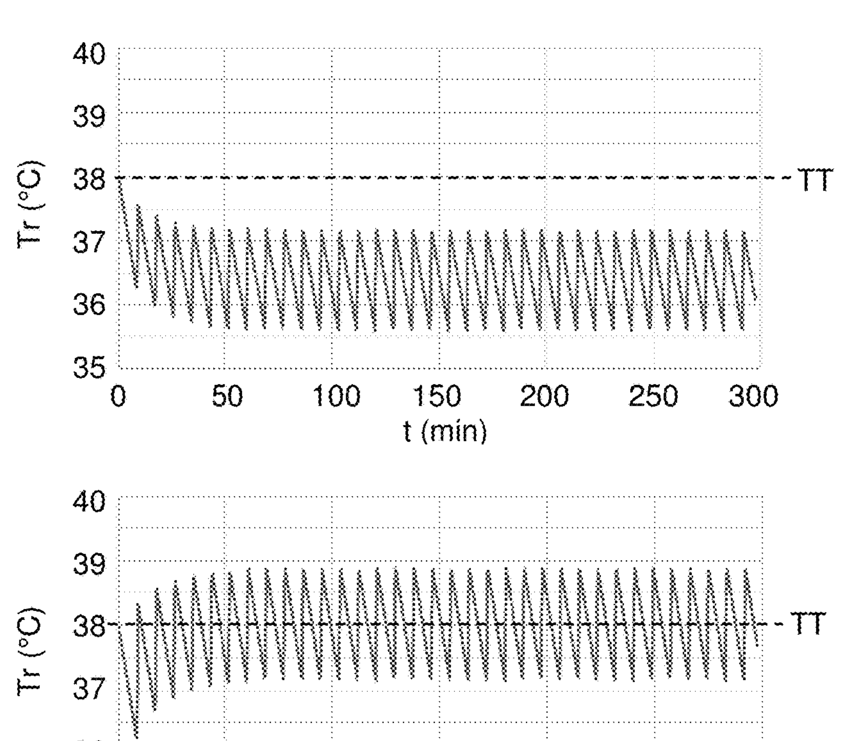
FIG. 7C
FIG. 7D
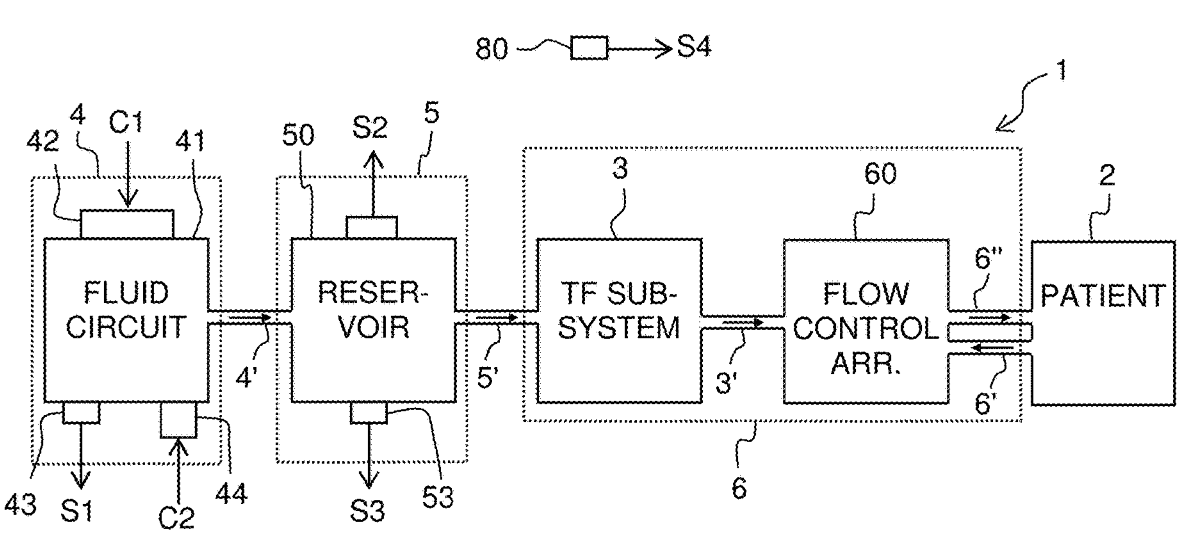
FIG. 8A

CONTROL OF FLUID TEMPERATURE IN A DIALYSIS SYSTEM

PRIORITY CLAIM

This application is a national phase entry of PCT Application No. PCT/EP2023/062009, filed May 5, 2023, which claims priority to Swedish Patent Application No. 2250594-5, filed on May 18, 2022, the entire disclosures of which are incorporated herein by reference.

TECHNICAL FIELD

The present disclosure relates to the field of dialysis and in particular to a technique of controlling the temperature of a fluid in a reservoir in a dialysis system.

BACKGROUND ART

Renal replacement therapy (RRT) is a therapy that replaces the normal blood-filtering function of the kidneys. It is used when the kidneys are not working well, which is known as kidney failure and includes acute kidney injury (AKI) and chronic kidney disease (CKD). RRT involves removal of water from the body of the patient suffering from kidney failure, as well as exchange of solutes with the body. One example of RRT is extracorporeal blood therapy, in which blood is circulated outside of the patient and interfaced with one or more medical fluids. Modalities of extracorporeal blood therapy include hemodialysis (HD), hemofiltration (HF) and hemodiafiltration (HDF). Another example of RRT is peritoneal dialysis (PD), in which a medical fluid is infused into the peritoneal cavity of the patient to interface with the blood of the patient through the peritoneal membrane.

RRT is performed by a dialysis system which is formed by arranging one or more disposable components on a dialysis machine.

Medical fluids used in HD and PD are commonly known as dialysis fluids. In HF, the medical fluid is known as replacement fluid, since it is infused into the blood of the patient to replace fluid removed during therapy. In HDF, both dialysis fluid and replacement fluid are used.

Extracorporeal blood therapy by HD, HF or HDF is performed differently for treatment of patients with AKI compared to patients with CKD, by use of a different type of dialysis machine. Generally, compared to CKD patients, AKI patients are treated continuously over a longer period of time and at lower fluid flow rates. Such continuous treatment is commonly known as CRRT (Continuous Renal Replacement Therapy). To ensure precise and consistent monitoring and control of fluid removal, known as ultrafiltration, AKI machines are typically provided with scales that are used for measuring the weight of fresh treatment fluid and the weight of spent treatment fluid during therapy. CKD machines instead use flow meters or volumetric pumping to control ultrafiltration.

PD machines, also known as cyclers, may include at least one scale to measure the weight of fresh treatment fluid infused into the peritoneal cavity and the weight of spent treatment fluid withdrawn from the peritoneal cavity. Alternatively, cyclers may use volumetric pumps to control ultrafiltration.

In the example of AKI, for example CRRT, treatment fluid is conventionally supplied from bags provided by a manufacturer. The bags are typically stored at room temperature and thus the treatment fluid will cool the blood of the patient during treatment. This may lead to hypothermia for the patient. Current mitigations are to pre-heat the bags, add an inline warmer of treatment fluid before meeting the blood, or add an inline warmer in the extracorporeal blood circuit. This adds complexity and cost to the AKI machine and/or increases the workload on the user.

These problems may be relevant to other types of RRT as well, depending on the requirements and configuration of the dialysis system.

SUMMARY

It is an objective to at least partly overcome one or more limitations of the prior art.

A further objective is to provide a technique for ensuring a consistent body temperature of the patient during RRT.

Another objective is to provide such a technique that is simple to implement on future and existing dialysis systems.

One or more of these objectives, as well as further objectives that may appear from the description below, are at least partly achieved by a dialysis system according to the independent claim, embodiments thereof being defined by the dependent claims.

A first aspect of the present disclosure is a dialysis system comprising: a supply sub-system, which is configured to supply a fluid and comprises a heating device for heating the fluid; a storage sub-system comprising a non-heated reservoir, wherein the non-heated reservoir is fluidly connected to receive said fluid from the supply sub-system and configured to hold an intermediate supply of the fluid during operation of the dialysis system; a treatment sub-system, which is configured to obtain the fluid from the storage sub-system and perform a dialysis treatment by use of the fluid; and a control device which is configured to operate the treatment sub-system to perform the dialysis treatment. The control device is further configured to operate the supply sub-system to perform a sequence of fluid supply cycles causing a sequence of time-separated boluses of said fluid to be supplied to the non-heated reservoir, wherein a respective fluid supply cycle among the fluid supply cycles is assigned a target temperature and comprises a predefined number of boluses, wherein the supply sub-system is operated to achieve, through said predefined number of boluses, the target temperature of the fluid in the non-heated reservoir for the respective fluid supply cycle.

The first aspect enables a target temperature of a fluid within a reservoir to be achieved without the use of dedicated heating equipment within or around the reservoir, such as an electrical heater. The reservoir is thus non-heated. In the absence of appropriate countermeasures, fluid held in a non-heated reservoir will lose heat to the surroundings and gradually cool down. The temperature of the fluid will thereby vary with the residence time of the fluid in the reservoir and may ultimately become too cold to be used in dialysis treatment. The foregoing aspects involve the countermeasure of supplying boluses of the fluid, which has been appropriately heated by a heating device in the supply sub-system, into the non-heated reservoir. The supply of boluses of heated fluid is a simple yet efficient technique of adjusting the temperature of the fluid in the non-heated reservoir. By stabilizing the fluid temperature at a target temperature, a consistent body temperature of the patient is ensured while dialysis treatment is performed by use of the fluid in the non-heated reservoir. The bolus-based technique is applicable to any type of reservoir, be it permanently installed in the storage sub-system or a disposable unit. Thus, the first aspect is simple to implement on any existing or future dialysis system.

In some embodiments, the target temperature is a temperature of the fluid in the non-heated reservoir at a target time point within the respective fluid supply cycle, or a time-average of the temperature of the fluid in the non-heated reservoir during the respective fluid supply cycle.

In some embodiments, the control device is configured to: obtain the target temperature; determine an energy content of the predefined number of boluses to attain the target temperature; and operate the supply sub-system to prepare, in accordance with the energy content, a fluid portion for use in generating the predefined number of boluses.

In some embodiments, the control device is configured to: determine a designated size of a respective bolus among the predefined number of boluses, and a designated temperature of the respective bolus that result in the predefined number of boluses having said energy content; operate the supply sub-system to heat the fluid portion to the designated temperature by use of the heating device; and operate the supply sub-system to generate the respective bolus with the designated size from the fluid portion that has the designated temperature.

In some embodiments, the control device is configured to: determine an amount of said fluid that is removed from the non-heated reservoir by the treatment sub-system during the respective fluid supply cycle; and determine the energy content of the predefined number of boluses partly based on the amount of said fluid that is removed from the non-heated reservoir.

In some embodiments, the control device is configured to determine the designated size of the respective bolus based on the amount of said fluid that is removed from the non-heated reservoir during the respective fluid supply cycle.

In some embodiments, the control device is configured to, based on the designated size of the respective bolus, determine the designated temperature of the respective bolus to achieve the energy content of the predefined number of boluses.

In some embodiments, the control device comprises a calculation model, which is configured to: estimate a total energy loss from the fluid in the non-heated reservoir during the respective fluid supply cycle; and determine the energy content of the predefined number of boluses based on the total energy loss during the respective fluid supply cycle.

In some embodiments, the total energy loss comprises a first loss portion that represents dissipated thermal energy from the fluid in the non-heated reservoir, and a second loss portion that represents energy loss by removal of the fluid from the non-heated reservoir by the treatment sub-system.

In some embodiments, the total energy loss further comprises a third loss portion that represents dissipated thermal energy from the fluid in a flow path, which extends from the supply sub-system to the non-heated reservoir.

In some embodiments, the control device is operable in a steady-state mode, in which the target temperature is identical for a plurality of consecutive fluid supply cycles, wherein the control device is configured, in the steady-state mode, to set the energy content of the predefined number of boluses equal to the total energy loss during the respective fluid supply cycle.

In some embodiments, the calculation model is configured to: calculate a momentary temperature of the fluid in the non-heated reservoir during the respective fluid supply cycle; and operate on the momentary temperature to determine the energy content of the predefined number of boluses so as to achieve the target temperature.

In some embodiments, the control device is configured to obtain a measured value, which is indicative of the momentary temperature of the fluid in the non-heated reservoir at a reference time point, and the calculation model is configured to calculate the momentary temperature of the fluid in the non-heated reservoir based on the measured value.

In some embodiments, the control device is configured to: obtain a further measured value, which is indicative of the momentary temperature of the fluid in the non-heated reservoir at a time point subsequent to the reference time point; and adjust a calculated momentary temperature at said time point and/or the calculation model based on the further measured value.

In some embodiments, the calculation model is further configured to: calculate a momentary heat dissipating area of the non-heated reservoir and/or a momentary amount of said fluid in the non-heated reservoir; and estimate the momentary temperature as a function of the momentary heat dissipating area and/or the momentary amount of said fluid in the non-heated reservoir.

In some embodiments, the control device is configured to obtain input data for use by the calculation model, said input data being indicative of a duration of the respective fluid supply cycle, a timing of the respective bolus within the respective fluid supply cycle, a duration of the respective bolus, and a time profile for removal of the fluid from the non-heated reservoir during the respective fluid supply cycle.

In some embodiments, the control device is configured to determine the time profile based on an operational setting of the treatment sub-system or a measured flow rate of the fluid into the treatment sub-system.

In some embodiments, wherein the respective bolus is supplied to the non-heated reservoir during a bolus period, wherein the calculation model comprises a function for estimating energy loss from the non-heated reservoir during the bolus period, said function accounting for change in energy loss caused by temperature change of the fluid in the non-heated reservoir as a result of the supply of the respective bolus.

In some embodiments, the control device is configured to operate the supply sub-system to perform the sequence of fluid supply cycles to impart, between consecutive boluses, a temperature decrease of less than approximately 5° C., 4° C., 3° C., 2° C. or 1° C. to the fluid in the non-heated reservoir.

In some embodiments, the control device is configured to operate the supply sub-system to perform the respective fluid supply cycle with a duration of more than 5, 10 or 15 minutes and less than 30, 60 or 120 minutes.

In some embodiments, the non-heated reservoir is a disposable component.

In some embodiments, the dialysis system further comprises an ambient sensor, which is arranged to measure an ambient temperature at the storage sub-system, and the control device is configured to determine the energy content of the predefined number of boluses based on the ambient temperature.

In some embodiments, the storage sub-system comprises a scale for measuring a weight of the non-heated reservoir, and the control device is configured to cause the supply sub-system to supply the respective bolus when the non-heated reservoir has a predefined weight, as measured by the scale.

In some embodiments, the control device is configured to perform open-loop control of the supply sub-system to achieve the target temperature.

In some embodiments, the dialysis system further comprises a measurement arrangement, which is configured to measure, for the fluid in the non-heated reservoir, a temperature value that corresponds to the target parameter, and the control device is configured to operate the supply sub-system to adjust, based on a difference between the target temperature and the measured temperature value, the size of the respective bolus and/or the temperature of the fluid that is to be supplied by the respective bolus.

In some embodiments, the fluid is a treatment fluid for use in the dialysis treatment.

In some embodiments, the fluid is water, and the treatment sub-system comprises a mixing arrangement which is configured to mix the fluid with one or more concentrates to provide a treatment fluid for use in the dialysis treatment.

A second aspect of the present disclosure is a control device as included in the dialysis system according to the first aspect or any of its embodiments.

A third aspect of the present disclosure is a computer-implemented method of operating a dialysis system comprising a supply sub-system, a storage sub-system, and a treatment sub-system. The method comprises: operating the treatment sub-system to obtain a fluid from a non-heated reservoir in the storage sub-system and perform a dialysis treatment by use of the fluid; and operating the supply sub-system to perform a sequence of fluid supply cycles causing a sequence of time-separated boluses of said fluid to be supplied to the non-heated reservoir, wherein a respective fluid supply cycle among the fluid supply cycles is assigned a target temperature and comprises a predefined number of boluses, wherein the supply sub-system is operated to achieve, through said predefined number of boluses, the target temperature of the fluid in the non-heated reservoir for the respective fluid supply cycle.

Any embodiment of the first aspect may be adapted as an embodiment of the third aspect.

A fourth aspect of the present disclosure is a computer-readable medium comprising computer instructions which, when executed by processing circuitry, cause the processing circuitry to perform the method of the third aspect or any of its embodiments.

Still other objectives, aspects and embodiments, as well as features and technical advantages, may appear from the following detailed description, from the attached claims as well as from the drawings.

BRIEF DESCRIPTION OF THE DRAWINGS

FIGS. 7C-7D are graphs of the change in fluid temperature caused by a step change in bolus temperature of −1° C. and +1° C., respectively.

FIG. 8A is a diagrammatic view of a dialysis system in accordance with a second configuration example.

DETAILED DESCRIPTION OF EXAMPLE EMBODIMENTS

Figure 1A:
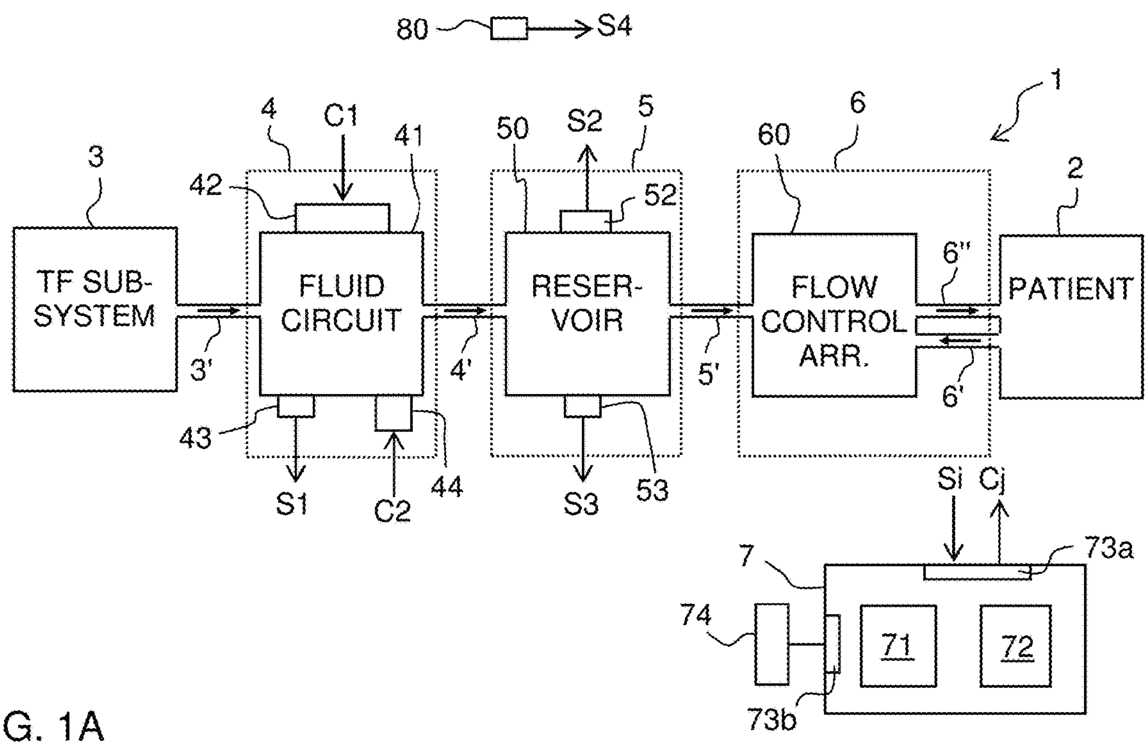
FIG. 1A is a diagrammatic view of a dialysis system in accordance with a first configuration example.

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure. As used herein, the terms "multiple", "plural" and "plurality" are intended to imply provision of two or more elements. The term "and/or" includes any and all combinations of one or more of the associated listed elements.

Well-known functions or structures may not be described in detail for brevity and/or clarity. Unless otherwise defined, all terms (including technical and scientific terms) used herein have the same meaning as commonly understood by one of ordinary skill in the art to which this disclosure belongs.

The present disclosure relates to a technique for controlling the temperature of a medical fluid for use in renal replacement therapy (RRT). As used herein, RRT refers to any therapy that replaces or supplements the normal blood-filtering function of the kidneys in a patient. RRT may involve removal of water from the blood of the patient, as well as exchange of solutes with the blood. RRT is also denoted "dialysis therapy" or dialysis treatment" herein. The technique for temperature control will be exemplified in the following with reference to hemodialysis (HD), although it is applicable to any modality of either extracorporeal blood therapy or peritoneal dialysis (PD).

The medical fluid may be any fluid that is consumed as part of RRT and is also referred to as "treatment fluid", abbreviated TF. In the context of extracorporeal blood therapy, the medical fluid may be dialysis fluid, which is interfaced with blood in a filtration unit, commonly known as a "dialyzer". Alternatively or additionally, the medical fluid may be so-called replacement fluid or substitution fluid, which is infused into the blood upstream or downstream of the dialyzer, for example as part of hemofiltration (HF) or hemodiafiltration (HDF), as is well known in the art. In the context of PD, the medical fluid may be dialysis fluid, which is infused into the peritoneal cavity of the patient and which interfaces with the blood of the patient through the peritoneal membrane that lines the peritoneal cavity.

Various embodiments will now be described with reference to FIG. 1A, which schematically illustrates an example dialysis system 1, which is fluidly connected to a patient 2 and operable to perform renal replacement therapy (RRT) on the patient 2. The dialysis system 1 comprises a plurality of sub-systems: a TF sub-system 3, a supply sub-system 4, a storage sub-system 5, and a treatment sub-system 6. The TF sub-system 3 is arranged to provide treatment fluid (TF) for use in the RRT. Depending on implementation, the TF sub-system 3 may comprise a bag of pre-made TF or an arrangement for generating TF by mixing purified water with one or more liquid or powdery concentrates, as is known in the art. A connecting path 3' extends between sub-systems 3, 4 to convey TF to the supply sub-system 4. The supply sub-system 4 is operable to condition and supply the TF for use in RRT. In the illustrated example, the supply sub-system 4 comprises a fluid circuit 41, a heating device ("heater") 42, a temperature sensor 43, and a pumping device 44. The fluid circuit 41 is fluidly connected to path 3'. The heater 42 is configured to heat at least a portion of the TF in the fluid circuit 41 to an operative temperature, as measured by the sensor 43. The pumping device 44 is configured to supply the heated TF to the storage sub-system 5 on a connecting path 4' that extends between the sub-systems 4, 5. As will be described in detail further below, the supply sub-system 4 is operable in a "bolus mode", in which the heated TF is intermittently supplied to the storage sub-system 5. In the illustrated example, the storage sub-system 5 comprises a reservoir 50, a weight scale 52, and a measurement arrangement 53. The reservoir 50 is configured receive the heated TF on path 4' and hold an intermediate supply of TF during operation of the dialysis system 1. The weight scale 52 is arranged to measure the weight (mass) of the reservoir 50 during on-going RRT, and the arrangement 53 is arranged to measure the temperature of the TF in the reservoir 50. As explained further below, the weight scale 52 and the arrangement 53 are optional. A connecting path 5' extends between sub-systems 5, 6 to convey TF from the reservoir 50 to the treatment sub-system 6. The treatment sub-system 6 is configured to obtain TF from the storage sub-system 5 and perform dialysis therapy by use of the TF, in accordance with conventional practice. The treatment sub-system 6 comprises a flow control arrangement 60, which is configured to obtain the TF on path 5' and distribute the TF in accordance with the RRT that is performed. In the example of extracorporeal blood therapy, the flow control arrangement 6 defines an extracorporeal blood circuit which is connected to receive blood from the patient 2, on path 6', and to return treated blood to the patient 2, on path 6". In the example of PD, the flow control arrangement 6 is configured to supply TF to the peritoneal cavity in the patient 2, on path 6', and receive spent TF from the peritoneal cavity, on path 6".

The dialysis system 1 may be implemented by one or more machine units and a disposable arrangement, in accordance with conventional practice. The disposable arrangement may comprise fluid lines and, in the example of extracorporeal blood therapy, a blood filtration unit ("dialyzer"). The disposable arrangement may be mechanically interfaced with the one or more machine units to form the dialysis system 1. The machine unit(s) may, for example, expose mechanical interfaces of pumps, clamps, sensors, etc.

As shown in FIG. 1A, a control device 7 is configured to control the operation of dialysis system 1. The control device 7 may be a controller in a machine unit in the dialysis system 1 or a separate controller. The control device 7 need not be unitary device but may be distributed among plural controllers in the system 1. The control device 7 is configured to receive measurement signals, represented as Si, and output control signals, represented as Cj. Although not shown in FIG. 1A, part of the measurement and control signals are used for controlling the treatment sub-system 6 to perform the RRT on the patient 2. Further, the control device 7 is configured to control the supply sub-system 4 by providing a control signal C1 to the heater 42, based on a measurement signal ("temperature signal") S1 from the temperature sensor 43, and a control signal C2 for the pumping device 44. As shown, the control device 7 may also receive a measurement signal ("weight signal") S2 from the weight scale 52, and a measurement signal ("temperature signal") S3 from the measurement arrangement 53. Further, the control device 7 may receive a measurement signal S4 from a temperature sensor 80 which is arranged to measure the ambient temperature ("room temperature") at the location of the dialysis system 1.

The control device 7 may be configured to generate the control signals Cj in accordance with a control program comprising computer instructions. The control program is also configured to operate based on the measurement signals Si. The control device 7 comprises processing circuitry 71 and computer memory 72. The control program is stored in the memory 72 and executed by the processing circuitry 71. The processing circuitry 71 may, for example, include one or more of a CPU ("Central Processing Unit"), a DSP ("Digital Signal Processor"), a GPU ("Graphics Processing Unit"), a microprocessor, a microcontroller, an ASIC ("Application-Specific Integrated Circuit"), a combination of discrete analog and/or digital components, or some other programmable logical device, such as an FPGA ("Field Programmable Gate Array"). The control program may be supplied to the control device 7 on a computer-readable medium, which may be a tangible (non-transitory) product (e.g., magnetic medium, optical disk, read-only memory, flash memory, etc.) or a propagating signal. In the illustrated example, the control device 7 comprises a signal interface 73*a* for providing control signals Cj and receiving measurement signals Si. The control device 7 also comprises a signal interface 73*b* for connection to a user interface (UI) device 74 which enables user interaction, for example input of control settings and output of feedback data. For example, the UI device 74 may comprise one or more of a keyboard, keypad, computer mouse, control button, printer, microphone, display device, indicator lamp, alarm device, speaker, touch screen, camera, voice control system, gesture control system, etc.

Figure 1B:
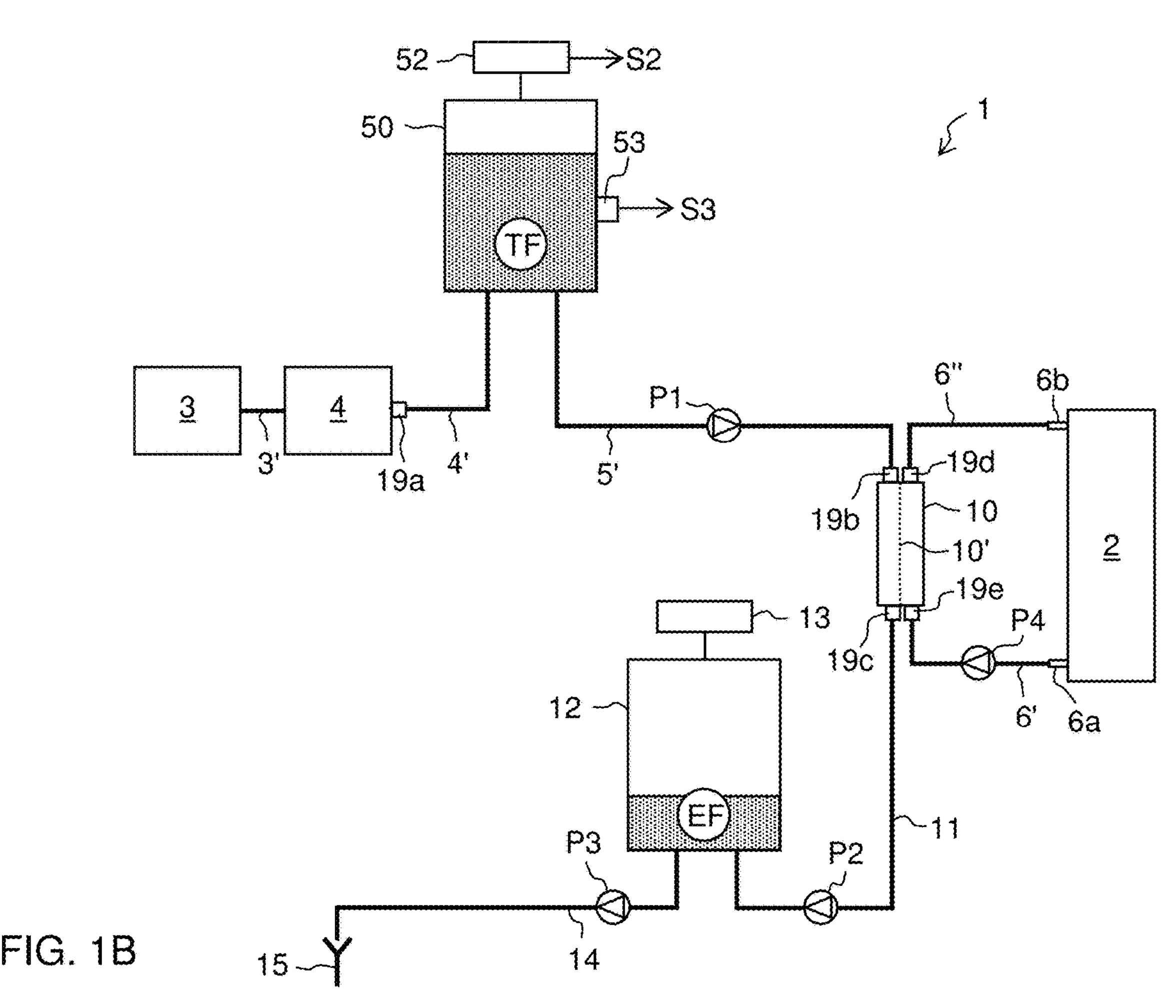
FIG. 1B shows an implementation of the dialysis system in FIG. 1A for hemodialysis by CRRT.

FIG. 1B is a schematic illustration of a dialysis system 1 for extracorporeal blood therapy by hemodialysis (HD), in a configuration commonly used for treatment of acute kidney injury (AKI), for example by CRRT. As explained in the following, the system 1 includes the sub-systems of FIG. 1A. Like in FIG. 1A, a TF sub-system 3 is fluidly connected, on path 3', to a supply sub-system 4, which is fluidly connected to a reservoir 50, on path 4'. The reservoir 50 is part of the storage sub-system 5 of FIG. 1A. The reservoir 50 is arranged on a scale 52. Instead of being hung from the scale 52, as shown, the reservoir may be placed to rest on the scale 52. The reservoir 50 may be a rigid or flexible container of any material, for example plastics. The reservoir 50 is arranged to hold an intermediate supply of treatment fluid, TF. In the illustrated example, a sensor 53 is arranged to measure the temperature of the TF in the reservoir 50. The sensor 53 may be of any type and may be attached to the outside of the reservoir 50 (as shown), arranged inside the reservoir 50, or be spaced from the reservoir 50. The sensor 53 may be arranged to measure an average temperature of the TF, for example by measuring the temperature at multiple locations. In some embodiments, the sensor 53 is an infrared thermometer, as known as non-contact thermometer.

The remaining components of the system 1 in FIG. 1B are part of the treatment sub-system 6 of FIG. 1A. Thus, in the example of FIG. 1B, the treatment sub-system 6 is fluidly connected to the reservoir 50 on path 5'. A fluid pump P1 is arranged in path 5' to pump TF from the reservoir 50 through a dialyzer 10. The dialyzer 10 is a conventional blood filter, in which a semipermeable membrane 10' is arranged to define a first chamber for TF and a second chamber for blood. One end of the first chamber is connected to receive TF on path 5'. The TF flows through the first chamber and leaves the dialyzer 10 at the opposite end. The TF that leaves the dialyzer 10 is "spent". To distinguish fresh TF from spent TF, the latter is denoted "effluent" herein and designated by EF. An effluent path 11 extends from the first chamber of the dialyzer 10 to an effluent (EF) reservoir 12. A fluid pump P2 is arranged in path 11 to pump EF into the reservoir 12. The reservoir 12 may be configured in correspondence with the reservoir 50 and is arranged on a scale 13. A drain path 14 extends from the reservoir 12 to a drain 15. A fluid pump P3 is arranged in path 14 to pump EF from the reservoir 12 to drain 15. The second chamber of the dialyzer 10 is arranged to receive blood from a withdrawal path 6', which is connected by a connector 6*a* to the patient 2. The second chamber of the dialyzer 10 is also in fluid communication with a return path 6", which extends to a connector 6*b*, which is connected to the patient 2. The connectors 6*a*, 6*b* are access devices (catheter, needle, etc.) in fluid communication with the circulatory system of the patient 2. A fluid pump P4 is arranged to pump blood from the patient 2 on the withdrawal path 6', through the second chamber of the dialyzer 10, and on the return path 6" back to the patient 2. When passing the second chamber, the blood is interfaced with the TF through the membrane 10' and thereby treated by hemodialysis. The principle of hemodialysis is well-known to the skilled person and will not be further explained herein. It should be appreciated that the example in FIG. 1B is simplified and that further conventional components may be included, such as clamps, pressure sensors, air detector, etc.

To perform HD therapy, the dialysis system 1 is operated to pump TF from reservoir 50 to the dialyzer 10 by pump P1 and to pump EF from the dialyzer by pump P2, and to pump blood through the dialyzer 10 by pump P4. During HD therapy, fluid is removed from the blood in correspondence to the difference in flow rates generated by the pumps P1, P2. The process of fluid removal is known as ultrafiltration in the art. In the illustrated example, and in accordance with conventional practice, the amount of ultrafiltration is precisely monitored based on the weights of the reservoirs 50, 12, as given by the scales 52, 13. However, a flow meter or volumetric pumping may instead be used to monitor the amount of treatment fluid supplied to the dialyzer 10 and the amount of effluent drawn from the dialyzer 10, respectively. During therapy, TF reservoir 50 is intermittently replenished, by the supply sub-system 4 being operated to supply TF. Further, the EF reservoir 12 may be intermittently drained in any suitable way. In the illustrated example, the pump P4 is operated to pump EF from the EF reservoir 12 to drain 15. In another example, the EF reservoir 12 is removed when full and replaced for an empty EF reservoir. In a further example, the dialysis system 1 comprises two EF reservoirs and is operated to direct the flow of EF into one EF container while the other EF container is being drained.

In the following description, it is presumed that the supply sub-system 5 lacks means for heating the TF in the reservoir 50. Thus, the reservoir 50 is "non-heated". While the TF is contained in the non-heated reservoir 50, it will lose heat to the surroundings and gradually cool down. It may be noted that it may be desirable to avoid frequent replenishment of the TF reservoir 50, since the monitoring of the ultrafiltration is rendered less precise during such replenishment. Thus, the residence time in the reservoir 50 may be considerable. For example, in CRRT, 5 liters of TF may be consumed in about 2 hours. Experiments indicate that a plastic bag that is initially filled with TF at 38° C. and left in for 2 hours in a room at 20° C. may contain TF at 28° C. after 2 hours. Under these circumstances, the patient will be subjected to significant cooling through the TF. Such cooling is detrimental to the health and comfort of the patient. For example, hypothermia in dialysis patients has been reported to cause shivering, loss of fine motor coordination, lethargy and mild confusion. Other reported consequences of hypothermia include immunosuppression with increased infection risk, cold diuresis, hypovolemia, electrolyte disorders, insulin resistance, impaired drug clearance, mild coagulopathy, cardiac problems, or even cardiac arrest.

A non-heated reservoir 50 may be used in the dialysis system 1 for a number of reasons. For one, the reservoir 50 may be non-heated by necessity, if an existing machine unit without heating capability is used as part of the dialysis system 1. Even if a new dialysis system 1 is developed it may be desirable for the reservoir 50 to be non-heated. For example, it may be difficult to achieve a uniform heating of the TF in the reservoir 50, and special care may need to be taken to avoid causing locally high temperatures that may have a negative impact on the TF. For example, TF that comprises bicarbonate is known to increasingly release carbon dioxide with increasing temperature. Also, for TF containing bicarbonate, precipitation may be aggravated with increasing temperature.

The temperature of TF in the reservoir 50 favors microbial growth. If the reservoir 50 is permanently installed in the dialysis system 1, it needs to be disinfected, for example between treatments. A complete disinfection may be difficult to ascertain if the volume of the reservoir 50 is large, and the disinfection may take considerable time if the reservoir 50 is designed for relatively small incoming and outgoing flow rates. It may therefore be desirable for the reservoir 50 to be part of the disposable arrangement, so that the reservoir 50 is replaced when deemed necessary, for example between treatments or at predefined intervals. Heating of such a disposable reservoir requires provision of a tailored heating device in the dialysis system 1, in order to achieve a complete and still gentle heating of TF in the disposable reservoir 50.

In the example of FIG. 1B, the reservoir 50 is part of a disposable arrangement, which is releasably connected to the supply sub-system 4. In FIG. 1B, the disposable arrangement comprises the fluid path 4', the reservoir 50, the fluid path 5', the effluent path 11, the reservoir 12, the drain path 14, the dialyzer 10, the withdrawal path 6', and the return path 6". The fluid paths 4', 5', 6', 6", 11, 14 may be defined by fluid lines (as shown) and/or fluid channels of a unitary structure such as a cassette. The fluid paths comprises connectors 19*a*, 19*b*, 19*c*, 19*d*, 19*e* for releasable engagement with corresponding connectors to establish a fluid connection. As is known in the art, the pumps P1, P2, P3, P4 may be peristaltic pumps that comprise a mechanical interface for engaging a dedicated segment of a fluid line. Alternatively, one or more of the pumps P1-P4 may be integrated into the disposable arrangement, for example in the form of a disposable membrane pump.

Figure 2A:
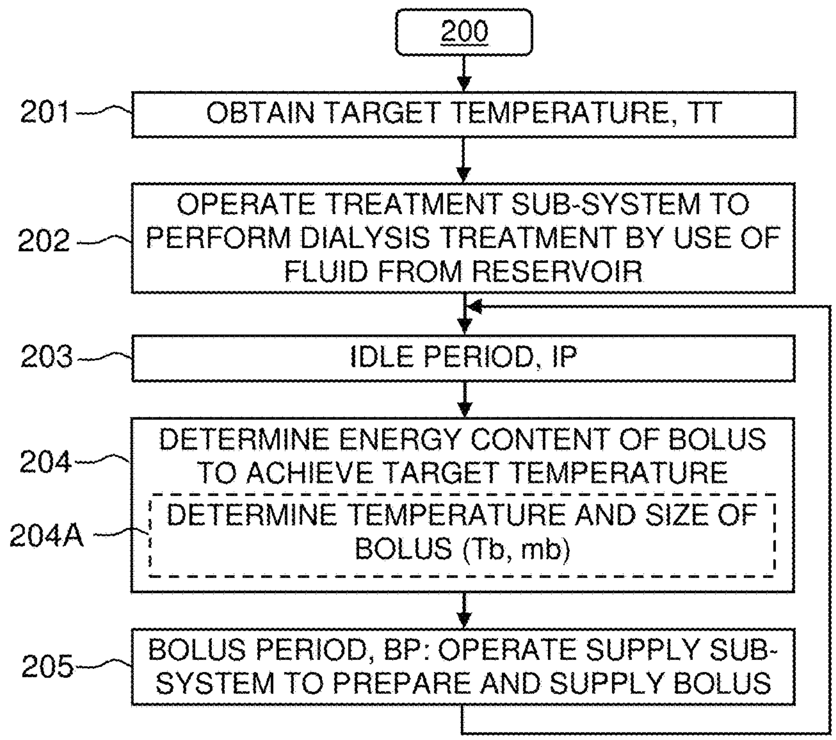
FIG. 2A is a flow chart of an example method of controlling the fluid temperature in a reservoir of a dialysis system.

FIG. 2A is a flow chart of an example method 200 which addresses the problem of maintaining and/or adjusting the temperature of a fluid in a non-heated reservoir. The method 200 will be described with reference to the dialysis system 1 in FIGS. 1A-1B and may be performed by the control device 7. The method 200 operates the supply sub-system 4 to perform a sequence of fluid supply cycles, where each fluid supply cycle involves a supply of at least one bolus of fluid to the non-heated reservoir 50. The respective bolus is supplied in a bolus period (BP). As used herein, a "bolus" denotes an amount of fluid that is supplied to the reservoir 50 during a confined time period. Thus, a bolus is an intermittently supplied amount of fluid. In the dialysis system 1 of FIGS. 1A-1B, the bolus contains heated TF. Consecutive BPs are separated by an idle period (IP), in which no fluid is supplied to the reservoir 50 by the supply sub-system 4. The number of boluses and the timing each BP and IP within the fluid supply cycle is predefined and thus known to the control device 7. A fluid supply cycle may include any number of BPs and IPs, and the respective BP may have any location (timing) within the fluid supply cycle.

Each fluid supply cycle is assigned a target temperature to be attained by the fluid in the reservoir 50. By the method 200, the supply sub-system 4 is operated to adjust the energy content of the respective bolus that is supplied during a fluid supply cycle so as to achieved the target temperature for this fluid supply cycle. In some embodiments, the energy content is at least partly adjusted by operating the heater 42 in the supply sub-system 4 (FIG. 1A).

Figure 2B:
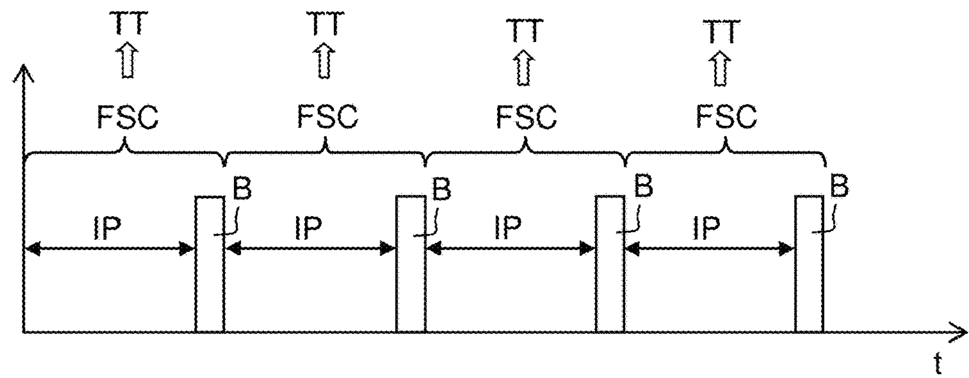
FIGS. 2B-2C show examples of fluid supply cycles.
Figure 2C:
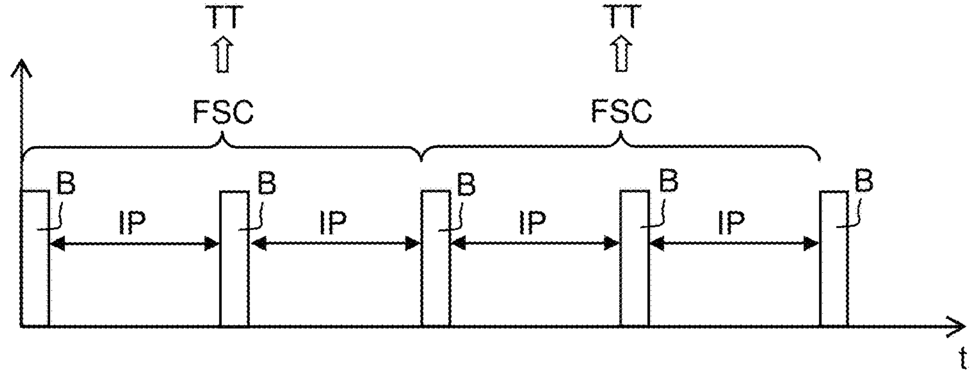

Two example sequences of fluid supply cycles are shown in FIGS. 2B-2C, which are timing diagrams for boluses, B, separated in time by idle periods, IP. Each fluid supply cycle, FSC, is assigned a target temperature, TT, to be achieved in the FSC. In FIG. 2B, each FSC involves a single bolus, B, and has an idle period, IP, before the bolus. In FIG. 2C, each FSC involves two boluses, B, each followed by a respective idle period, IP.

In the following non-limiting examples, the method 200 will be presented and explained for a fluid supply cycle containing a single IP and a single BP, with the IP preceding the BP, as shown in FIG. 2A. It is to be understood that the following description is generally applicable to other definitions of the fluid supply cycle, with respect to the number of boluses and the timing of the respective bolus within the fluid supply cycle.

In step 201, a target temperature is obtained. The target temperature (TT) may be given by any metric that represents a temperature of the fluid in the reservoir 50 during the fluid supply cycle. In some embodiments, TT is a temperature at a selected time point ("target time point") within the fluid supply cycle, for example at the start or end of an IP or a BP. In some embodiments, TT is a time-average of the fluid temperature in the reservoir 50 during the fluid supply cycle, or part thereof. In the examples below, TT is the fluid temperature at the end of the BP. The target temperature may be entered by the user via the UI device 74 or may be retrieved as a predefined setting from memory 72. It is also conceivable that the user is allowed to enter a desired temperature downstream of the reservoir 50, for example the temperature of the TF that enters the dialyzer 10 or the temperature of the blood downstream of the dialyzer 10. In such variants, the control device 7 is configured to recalculate the desired temperature into a target temperature of the fluid in the reservoir 50, by accounting for energy losses downstream of the reservoir 50.

In step 202, the treatment sub-system 6 is operated to perform dialysis therapy during a treatment session while obtaining TF from the reservoir 50, for example as described herein above. In some embodiments, step 202 is continuously performed during all of the subsequent steps 203-205. In a variant, dialysis therapy is paused during BP (step 205, below), which means that TF is not removed from the reservoir 50 during BP.

Although not shown in FIG. 2A, the method 400 comprises a step of operating the supply sub-system 4 to fill a predefined amount of fluid at a predefined temperature into the reservoir 50 before the treatment session is initiated in step 202. The predefined temperature may be set in view of the target temperature.

The sequence of steps 203-205 are repeatedly performed to generate the above-mentioned sequence of fluid supply cycles. In step 203, the supply sub-system 4 is operated to not supply TF to the reservoir 50 on fluid path 4'. Step 203 thus results in an idle period, IP. In step 204, a required energy content of the bolus to be supplied in the subsequent bolus period is determined. The required energy content is determined so as to achieve the target temperature in the fluid supply cycle. In step 205, the supply sub-system 4 is operated to prepare and supply a bolus of TF with the required energy content. Step 205 thus results in a bolus period, BP.

The method 200 provides the technical advantage of achieving the target temperature in the fluid within the reservoir 50 without the need to install a dedicated heating device within or around the reservoir 50. Further, the use of fluid supply cycles for heating the fluid in the reservoir 50 inherently involves a gentle heating. If TF is known to be degraded at temperatures above a temperature limit, the temperature of the bolus will be maintained below this temperature limit, and consequently the fluid in the reservoir 50 will not be subjected to temperatures above the temperature limit when the bolus is supplied.

It should be noted that step 204 need not be performed for every repetition of steps 203-205. In some embodiments, step 204 is performed during a subset of the fluid supply cycles. In some embodiments, step 204 is performed in advance of the sequence of fluid supply cycles, i.e. before the repeating sequence of steps 203, 205 is initiated.

In some embodiments, as indicated by dashed lines in FIG. 2A, step 204 comprises a step 204A of configuring the bolus to have the required energy content by determining a designated size and a designated temperature of the bolus. The designated size may be given as volume or mass. In the following, the designated size of the bolus is denoted bolus mass (mb). The designated temperature of the bolus is denoted bolus temperature (Tb).

In step 205, the control device 7 operates the supply sub-system 4 to execute the bolus period by use of the control signals C1, C2. The control device 7 generates the control signal C1, based on the temperature signal S1, to operate the heater 42 to heat a fluid portion of treatment fluid to Tb, and generates the control signal C2 to operate the pumping device 44 to supply at least part of the heated fluid portion during the bolus period.

In some embodiments, step 204A comprises determining the bolus mass based on the weight signal S2 from the scale 52, which represents the weight of the reservoir 50 and thus is indicative of the momentary fluid mass in the reservoir 50.

In some embodiments, step 204A comprises determining the bolus temperature based on the temperature signal S3 from the sensor 53, which represents the temperature of the fluid in the reservoir 50. However, in some embodiments, the sensor 53 is omitted, for example to reduce complexity and/or cost. In such embodiments, the fluid temperature in the reservoir 50 may be estimated by use of a calculation model of the energy loss from the reservoir 50, as will be described further below.

Figure 3A:
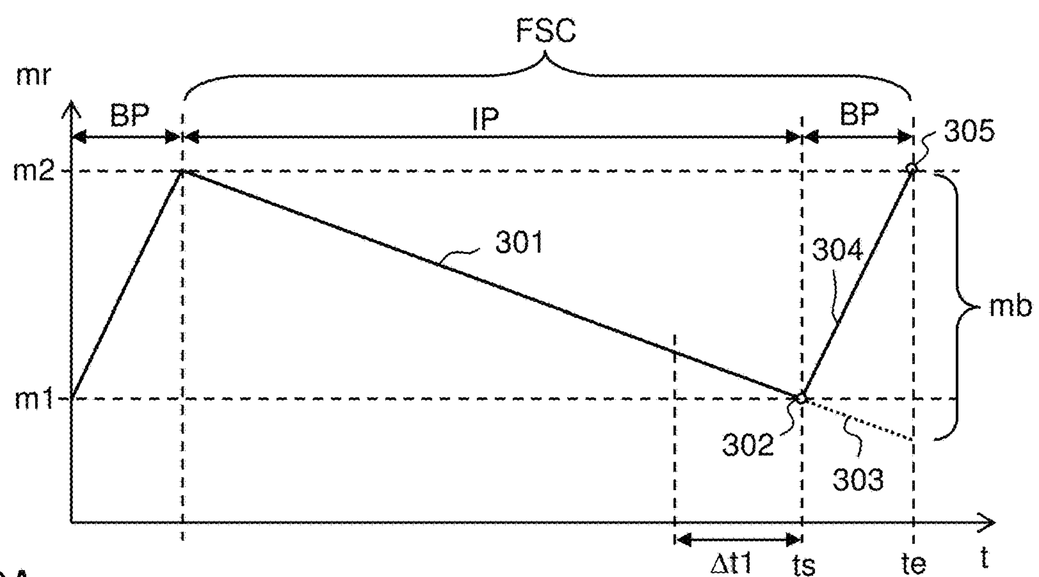
FIGS. 3A-3B show time profiles of fluid weight and fluid temperature, respectively, in a reservoir in a dialysis system during the method of FIG. 2.

FIG. 3A is an example graph of fluid mass (mr) in the reservoir 50 as a function of time (t). Specifically, FIG. 3A illustrates mr during a sequence of BP-IP-BP as performed by the method 200. Here, a fluid supply cycle (FSC) is defined by an IP followed by a BP. Time ts represents the start of BP, and time the represents the end of BP. In the example of FIG. 3A, the treatment sub-system 6 consumes TF at a constant flow rate during both IP and BP. Thus, as indicated by line 301, mr decreases linearly during IP from m2 at start of IP. At point 302, which corresponds to the start of BP, mr is m1. As indicated by line 304, a bolus is supplied to the reservoir 50 during BP, resulting in an increased fluid mass. In the illustrated example, the method 200 is performed to restore the fluid mass during each fluid supply cycle. Thus, at the end of BP (point 305), mr is m2. Since fluid is also removed from the reservoir during BP, as indicated by dotted line 303, the bolus mass mb is determined (step 204A) to match the total fluid removal during the fluid supply cycle, FSC.

Figure 3B:
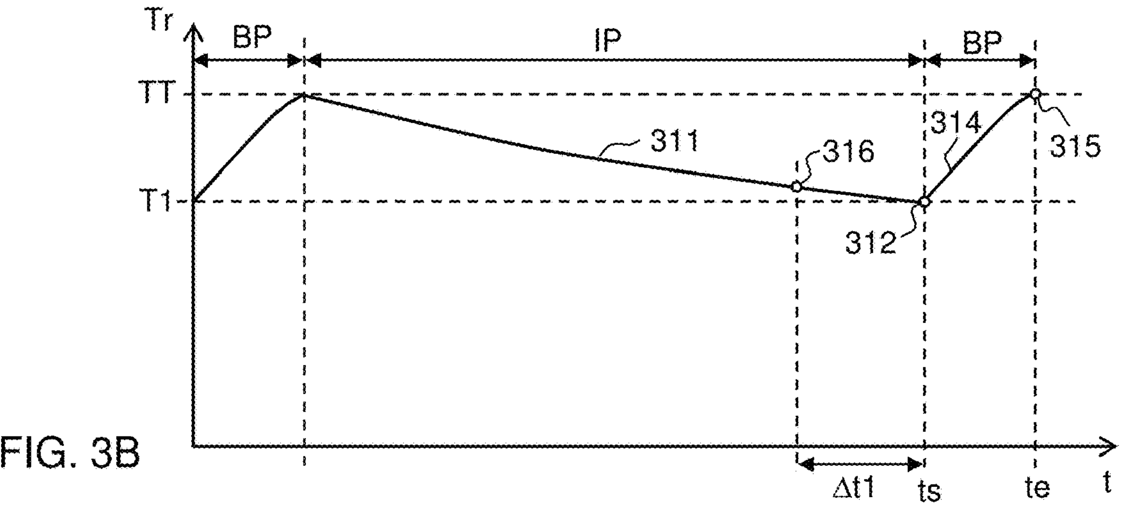

FIG. 3B is a corresponding example graph of fluid temperature (Tr) in the reservoir 50 during the sequence BP-IP-BP. In the example of FIG. 3B, it is assumed that the target temperature TT defines the fluid temperature at the end of BP. As indicated by line 311, the temperature decreases during IP. The temperature decrease is caused by dissipation of thermal energy to the surroundings of the reservoir 5, as well as the removal of fluid by the treatment sub-system 6. At point 312, which corresponds to the start of BP, Tr is T1. As indicated by line 314, Tr increases as the bolus is supplied to the reservoir 50 during BP. At the end of BP (point 315), Tr has reached the target temperature TT.

Reverting to step 204 in FIG. 2A, the required energy content of the respective bolus may be determined based on an estimation or simulation of the energy loss from the fluid in the reservoir 50 during one or more fluid supply cycles. If step 204 is performed in advance of the sequence of fluid supply cycles, the estimation extends over a plurality of subsequent fluid supply cycles. If step 204 is performed during an on-going fluid supply cycle, the estimation extends over at least the on-going fluid supply cycle. Examples of the estimation are given below with reference to FIGS. 4A-4E.

In step 205, the control device 7 may prepare a fluid portion for use in generating the bolus, in accordance with the required energy content given by step 204. In the example of FIG. 3B, point 316 designates a time point when the control device 7 starts to prepare the fluid portion. It is realized that a preparation time Δt1 may be needed to heat a fluid portion to the bolus temperature (Tb), for example if the bolus temperature differs from the bolus temperature in the preceding fluid supply cycle and/or if the heater 42 (FIG. 1A) is deactivated between bolus periods to save energy. The preparation time Δt1 may be predefined or determined dynamically by the control device 7, for example based on temperature signal S1. It is realized that step 204 may also need to be completed at point 316, for the bolus temperature to be known.

Figure 3C:
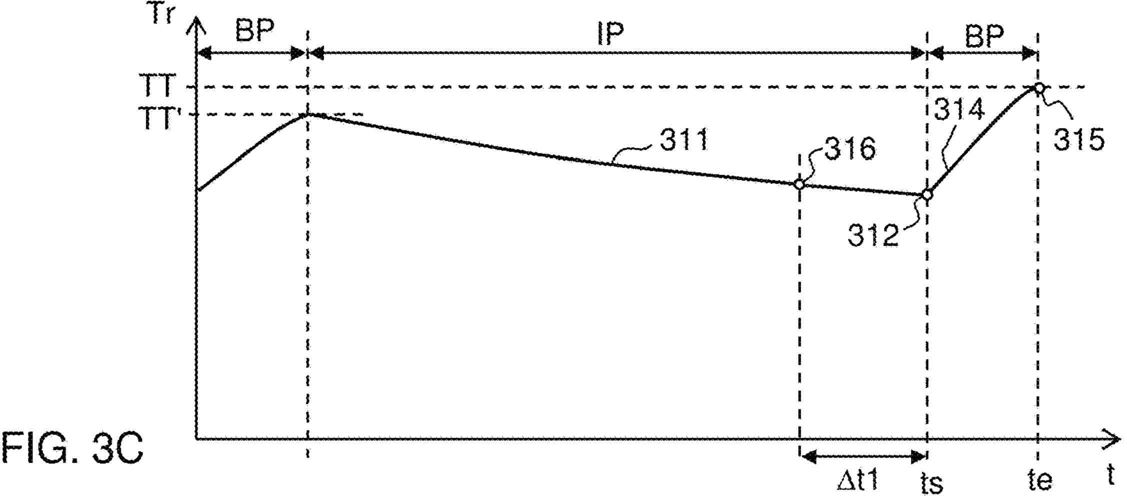
FIG. 3C shows another example of a time profile of fluid temperature.

In the example of FIG. 2A, the target temperature is set in step 201 before start of dialysis therapy and remains the same throughout the dialysis therapy performed by step 202. It is also conceivable that the target temperature is defined to change in accordance with a predefined time profile during dialysis therapy. For example, the time profile may be entered by the user via the UI device 74 before start of dialysis therapy. Thereby, the target temperature may change between fluid supply cycles. In another variant, the user may be allowed to adjust the target temperature during on-going dialysis therapy, which also results in a change in target temperature between fluid supply cycles. FIG. 3C corresponds to FIG. 3B and illustrates a scenario in which the target temperature is increased from TT' for a preceding cycle to TT for a current cycle.

Reverting to steps 204-205 in FIG. 2A, the required energy content of the bolus may be achieved by adjusting the bolus mass (mb), the bolus temperature (Tb), or both. Adjustment of both mb and Tb provides the potential advantage of improving the flexibility in achieving the required energy content. However, the flexibility in adjusting mb may be limited by other considerations. For example, mb may be set to attain a predefined target value of the fluid mass (mr) in the reservoir after the BP. In the example of FIG. 3A, the target mass is the same for each fluid supply cycle, so that the reservoir 50 is refilled to the same level. Generally, this means that the required energy content of the bolus is determined partly based on the amount of fluid that is removed ("total fluid removal") from the non-heated reservoir 50 during the fluid supply cycle. In some embodiments, the total fluid removal is given by control settings for the treatment sub-system 6. Alternatively or additionally, the control device 7 may estimate the total fluid removal based on measurements, for example the weight signal S2 from scale 52.

It is thus realized that the bolus mass (mb) may be given by the total fluid removal during the fluid supply cycle, and that the bolus temperature (Tb) may be determined so that the combination of bolus mass and bolus temperature corresponds to the required energy content of the bolus. As will be shown in relation to FIGS. 4A-4F, calculations in step 204 may be simplified when the bolus mass is known and only the bolus temperature is adjusted to meet the required energy content.

Figure 4A:
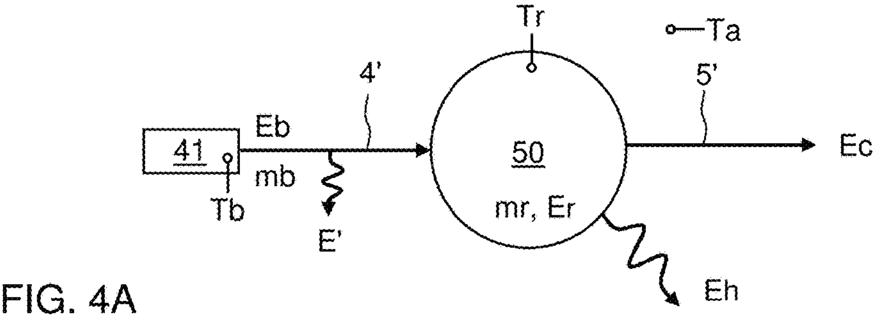
FIG. 4A illustrates calculation parameters for use in embodiments of the method in FIG. 2A, FIGS. 4B-4E are block diagrams of control circuitry comprising example calculation models for estimating energy loss.

In some embodiments, step 204 comprises estimating a total energy loss from the fluid in the reservoir 50 during the respective fluid supply cycle, and determining the required energy content of the bolus based on the total energy loss. A calculation model may be used to estimate the total energy loss. FIG. 4A illustrates various variables that may be included in such a calculation model. FIG. 4A shows the fluid circuit 41 of the supply sub-system 4, the connecting path 4', the reservoir 50, and the connecting path 5'. The variables include ambient temperate Ta, fluid temperature Tr in the reservoir, bolus temperature Tb, bolus mass mb, and fluid mass mr in the reservoir. The variables further include an energy content Er of the fluid in the reservoir, an energy loss Eh by dissipation from the fluid in the reservoir, an energy loss Ec by the removal ("consumption") of fluid from the reservoir by the treatment sub-system 6 on path 5', and an energy loss E' by dissipation from the fluid in path 4'. The total energy loss is given by the sum of Eh, Ec and E'. It may be noted that E' may be omitted if deemed to be insignificant, for example of the path 4' is short. As used herein, "dissipation" refers to energy that is lost by heat transfer to the surroundings and may, depending on implementation, include thermal conduction, thermal convection, or thermal radiation, or any combination thereof.

The calculation model is based on a set of equations that may be derived analytically and/or empirically. Appendix A comprises an example of equations that are derived analytically to describe the energy loss from the fluid based on the variables depicted in FIG. 4A.

Figure 4B:
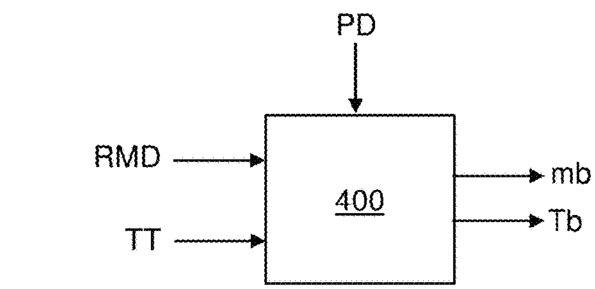
FIG. 4F is a flow chart of an example control procedure for use in the method of FIG. 2A.

FIGS. 4B-4E show examples of how a calculation model may be used by the control device 7 to determine the bolus mass (mb) and the bolus temperature (Tb) in accordance with step 204A. FIG. 4B is a block diagram of an example calculation model 400 in the control device 7. The calculation model 400 may be implemented by software executed by the processing circuitry 71 and/or by a dedicated part of the processing circuitry 71. The calculation model 400 is configured to input and operate on the target temperature TT, property data PD, and reference measurement data RMD to determine and output bolus mass mb and bolus temperature Tb for the respective fluid supply cycle. The property data, PD, defines the operation of the dialysis system 1, for example the fluid removal rate from the reservoir, the timing of the bolus period within the fluid supply cycle, the fluid supply rate of the bolus during the bolus period, etc. The reference measurement data, RMD, comprises measurement values of one or more of the variables in FIG. 4A at one or more reference time points before or during the fluid supply cycles, for example Tr, mr, Ta, etc.

FIG. 4C shows a more detailed example of the calculation model 400 in FIG. 4B. The calculation model 400 comprises first and second calculation blocks 410, 411, which operate on PD and RMD. The first block 411 is configured to calculate the energy loss during the idle period, denoted $E_{lossIP}$. The second block 411 is configured to calculate the energy loss during the bolus period, denoted $E_{lossBP}$. Both blocks 410, 411 are configured to estimate the energy loss caused by dissipation as well as by fluid removal. An example of functions used by the blocks 410, 411 is given in Appendix A. The functions in Appendix A are analytically determined and omit the energy loss E' in FIG. 4A. It is straight-forward to also include E'. As noted in Appendix A, the respective function may instead be at least partly empirically determined. The calculation model 400 further comprises a third block 415, which is configured to determine the required energy content of the bolus in view of the target temperature, $E_{lossIP}$, and $E_{lossBP}$. Based on the required energy content, block 415 determines and outputs mb and Tb. Block 415 may also account for any constraints imposed on mb and/or Tb, for example a maximum limit for Tb, or that mb should match the total fluid removal during the fluid supply cycle.

In some embodiments, the calculation model 400 is configured to perform an iterative calculation to determine mb and Tb. The iterative calculation is indicated by a dashed arrow from block 415 to block 411 in FIG. 4C. The iterative calculation may be implemented to account for the fact that the momentary temperature of the fluid in the reservoir (Tr) during the bolus period will not only depend on the momentary energy added by the bolus but also on the momentary energy loss, which in turn depends on Tr. It may be noted that the iterative calculation may be obviated if the second function used by block 411 is at least partly empirically determined to approximate the energy loss during the bolus period, for example based on Tr at the start and end of the bolus period (cf. points 312, 315 in FIGS. 3B-3C).

Figure 4D:
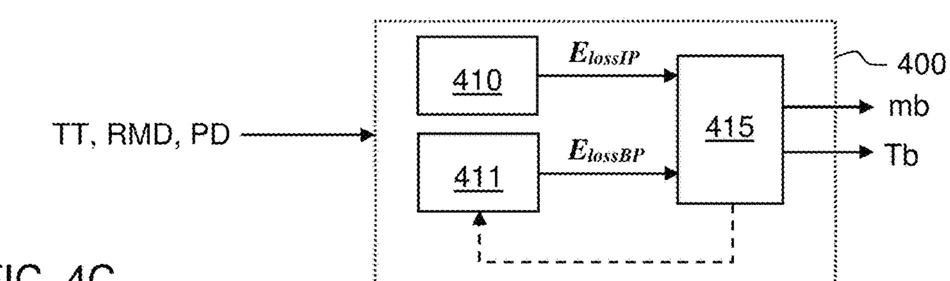
Figure 4D:
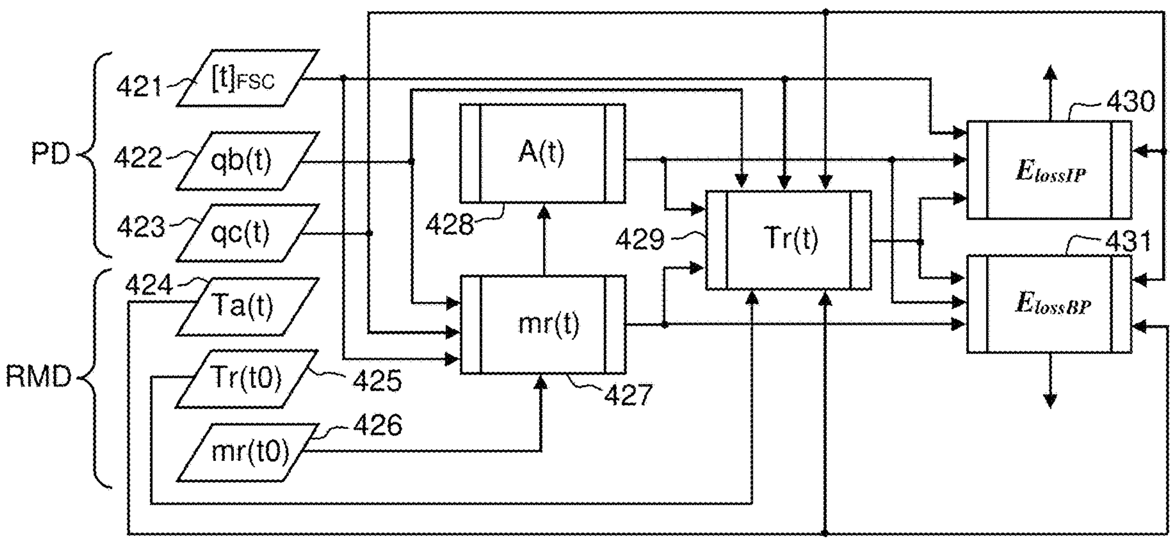

FIG. 4D is a functional diagram of an example implementation of blocks 410-411 in FIG. 4C in accordance with Appendix A. In the illustrated example, the property data (PD) comprises timing data ($[t]_{FSC}$) 421, which defines the timing the bolus period during the fluid supply cycle. In the example of FIGS. 3A-3C, the timing data 421 may indicate time points ts, the in relation to the start of the fluid supply cycle. PD further comprises a bolus time profile (qb(t)) 422, which defines the bolus flow rate as a function of time during the bolus period. The aggregated bolus flow during the bolus period equals mb. In one example, the bolus time profile 422 may be given by a constant value during the bolus period. PD further comprises a removal time profile (qc(t)) 423, which defines the fluid removal rate from the reservoir as a function of time during the fluid supply cycle. As noted above, the removal time profile 423 may be given by settings for the treatment sub-supply 6 and/or estimated based on the weight signal S2.

In the example of FIG. 4D, the reference measurement data (RMD) comprises ambient temperature (Ta(t)) 424, which is measured by the sensor 80 (FIG. 1A) at one or more time points before or during the dialysis therapy. RMD further comprises a measured value 425 of fluid temperature in the reservoir at a first reference time point, Tr(t0). In Appendix A, Tr(t0) is denoted $T_0$. If the reservoir 50 is associated with a temperature sensor (cf. 53 in FIG. 1A), Tr(t0) may be obtained from this temperature sensor at any time point before or during the dialysis therapy. Otherwise, Tr(t0) may be inferred from the temperature of the fluid that is supplied to the reservoir 50 by the supply sub-system 4 before the dialysis therapy is initiated. In another alternative, the supply sub-system 4 may be operative to draw fluid from the reservoir 50 and measure the temperature of the fluid, for example by the sensor 43. In a further alternative, Tr(t0) may be inferred from a temperature value measured by a sensor located downstream of the reservoir 50, for example in path 5' downstream of pump P1 in FIG. 1B or in path 6". The skilled person realizes that such a temperature value may be converted into a fluid temperature in the reservoir 50 by estimating and accounting for the energy loss between the reservoir and the sensor.

In FIG. 4D, RMD further comprises a measured value 426 of the fluid mass in the reservoir at a second reference time point, mr(t0). The first and second reference time points may or may not differ. It is also conceivable that the RDM comprises Tr and/or mr measured at more than one reference time point.

For simplicity of notation and in correspondence with Appendix A, qb(t), qc(t) and Ta(t) are assumed to be constants (time-invariant). The implementation in FIG. 4D comprises a plurality of time-dependent functions 427-431, which are evaluated based on the PD and RMD. Function 427 is operable to estimate the momentary fluid mass in the reservoir at any time point t, mr(t). With reference to Appendix A, function 427 may be performed in accordance with Eq. 4 during the idle period and Eq. 8 during the bolus period. Function 428 is operable to estimate the heat dissipating area of the fluid in the reservoir at any time point, A(t). With reference to Appendix A, function 428 may be performed in accordance with Eq. 5 during the idle period and Eq. 9 during the bolus period. As seen, function 428 operates on the output of function 427. However, as noted in Appendix A, other equations may be developed for use in function 428. In another alternative, the heat dissipating area is set to a constant (time-invariant) value. Function 429 is operable to estimate the fluid temperature in the reservoir at any time point, Tr(t). With reference to Appendix A, function 429 may be performed in accordance with Eq. 14 or a corresponding equation. As seen, function 429 operates on the output of function 427 (momentary fluid mass) and function 428 (momentary heat dissipating area). Function 430 is operable to estimate $E_{lossIP}$. With reference to Appendix A, function 430 may be performed in accordance Eq. 7. As seen, function 430 operates on the output of function 428 (momentary heat dissipating area) and function 429 (momentary temperature). Function 431 is operable to estimate $E_{lossBP}$. With reference to Appendix A, function 431 may be performed in accordance Eq. 15. As seen, function 431 operates on the output of function 427 (momentary fluid mass), function 428 (momentary heat dissipating area) and function 429 (momentary temperature). The output of functions 430, 431 corresponds to the output of blocks 410, 411 in FIG. 4C.

Figure 4E:
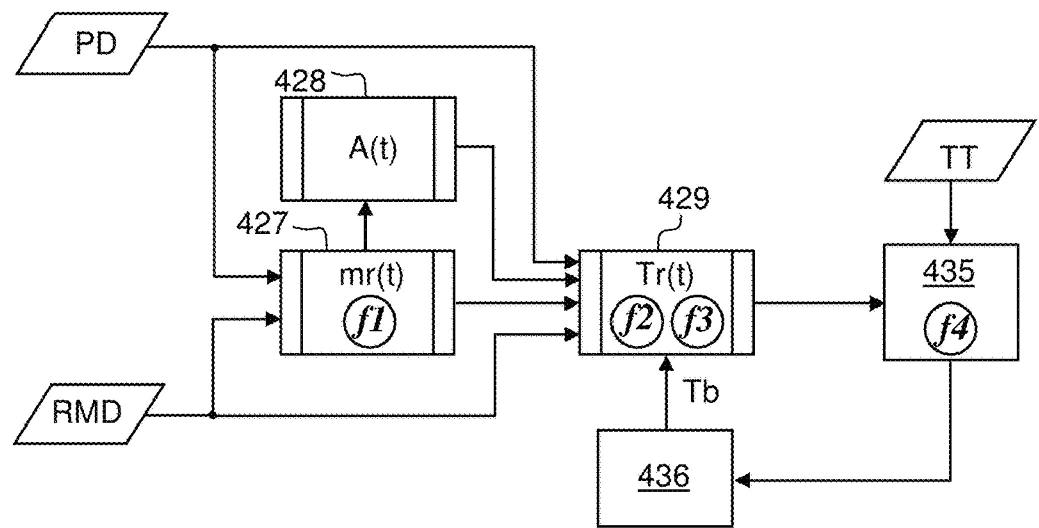

As understood from Appendix A, one or more of the functions in the calculation model 400 may depend on Tb and/or mb. Thereby, the calculation model may involve iterative calculations to derive Tb and/or mb, based on the target temperature TT. The iterative calculations may be implemented in many different ways. A non-limiting example is shown in FIG. 4E. The calculation model in FIG. 4E is based on a re-arrangement of the equations in Appendix A into the following sub-functions:

$$m_r(t) = f1(m_r(t_0), q_c, q_b, ts, t)$$

$$T_{r,IP}(t) = f2(m_r(t), T_0, t)$$

$$T_{r,BP}(t) = f3(T_{r,IP}(ts), q_c, q_b, m_r(t_0), T_b, t)$$

where $T_{r,IP}(t)$ and $T_{r,BP}(t)$ designate the fluid temperature in the reservoir during IP and BP, respectively. Further, the calculation model comprises a sub-function for calculating a current value of the target temperature:

$$TTa = f4(T_{r,IP}(t), T_{r,BP}(t))$$

It is realized that f4 depends on the definition of the target temperature and need not depend on both $T_{r,IP}(t)$ and $T_{r,BP}(t)$. For example if the target temperature is the fluid temperature at the end of the bolus period, f4 depends on $T_{r,BP}(t)$ only.

For simplicity, the dependence on PD and RMD is only schematically indicated in FIG. 4E and may be similar to FIG. 4D. Function 428 may be as described for FIG. 4D. Function 427 comprises f1 for calculating mr(t), and function 429 comprises f2 and f3 for calculating Tr(t) during IP and BP, respectively. Since f3 is dependent on Tb, the calculation model comprises a block 436, which is configured to provide a value of Tb to function 429 for use in calculation of Tr(t). The calculation model further comprises a block 435, which operates f4 to calculate TTa and provides an error signal indicative of the difference between TTa and TT to block 436. Block 436 comprises a conventional optimization algorithm for determining a new value of Tb based on the error signal. Thus, block 436 starts by providing an initial value of Tb, and then repeatedly, based on the error signal, optimizes Tb to minimize the difference between TTa and TT. When the difference fulfills a convergence criterion, block 436 outputs Tb. The example in FIG. 4E presumes that mb is known, but may be modified to determine mb as well.

FIGS. 4A-4E are specific examples of more generic embodiments of the calculation model. In one embodiment, the calculation model 400 is configured to calculate the momentary fluid temperature in the reservoir 50 during the respective fluid supply cycle (cf. Tr(t)), and operate on the momentary fluid temperature to determine the energy content of the bolus ("required energy content") so as to achieve the target temperature (TT). The calculation of the momentary fluid temperature provides an efficient way of determining the required energy content and facilitates evaluating TT fulfillment. In one embodiment, the control device 7 is configured to obtain a measured value of the momentary fluid temperature in the reservoir 50 at a reference time point (cf. mr(t0)), and the calculation model 400 is configured to calculate the momentary fluid temperature in the reservoir 50 based on the measured value. The use of the measured value provides a simple way of estimating the momentary fluid temperature, in which the measured value forms an anchor value or starting value for the calculation of the momentary fluid temperature at other time points. In one embodiment, the calculation model 400 is configured to calculate a momentary heat dissipating area of the reservoir 50 (cf. A(t)) and/or a momentary fluid amount in the reservoir 50 (cf. mr(t)), and estimate the momentary fluid temperature as a function of the momentary heat dissipating area and/or the momentary fluid amount in the reservoir 50. As noted above, the momentary fluid amount may alternatively be known and/or measured, and the heat dissipating area may alternatively be set to a constant value and/or be determined empirically. The accuracy of Tr(t) may be significantly improved by calculating A(t), for example as a function of mr(t), instead of using a constant value. Further, by calculating mr(t), the calculation of Tr(t) is rendered less dependent on measurement errors and/or predefined settings. In one embodiment, the control device 7 is configured to obtain input data for use by the calculation model 400, where the input data is indicative of a duration of the respective fluid supply cycle, a timing of BP within the respective fluid supply cycle (cf. ts), a duration of BP (cf. difference between ts and the), and a time profile for fluid removal from the reservoir 50 during the respective fluid supply cycle (cf. qc(t)). As noted above, qc(t) may be given by an operational setting of the treatment sub-system 6 or a measured flow rate of the fluid into the treatment sub-system 6. In one embodiment, the calculation model 400 comprises a function for estimating energy loss from the reservoir 50 during BP (cf. $E_{lossBP}$), which accounts for temperature changes of the fluid in the reservoir 50 caused by the supply of the bolus. While such a function may increase the complexity of the calculation model 400, it will also improve the accuracy of the calculations and ultimately improve the control of fluid temperature in the reservoir 50.

With reference to FIG. 3B, in which the target temperature (TT) is identical for a plurality of consecutive fluid supply cycles, the control device 7 may be operated in a "steady-state mode", in which the required energy content of the bolus for the respective fluid supply cycle is set equal to the total energy loss during this fluid supply cycle. This may significantly simplify the calculations of mb and/or Tb. For example, if mb is known and as long as the ambient temperature is unchanged, Tb will be same for every bolus in a sequence of fluid supply cycles.

Figure 4F:
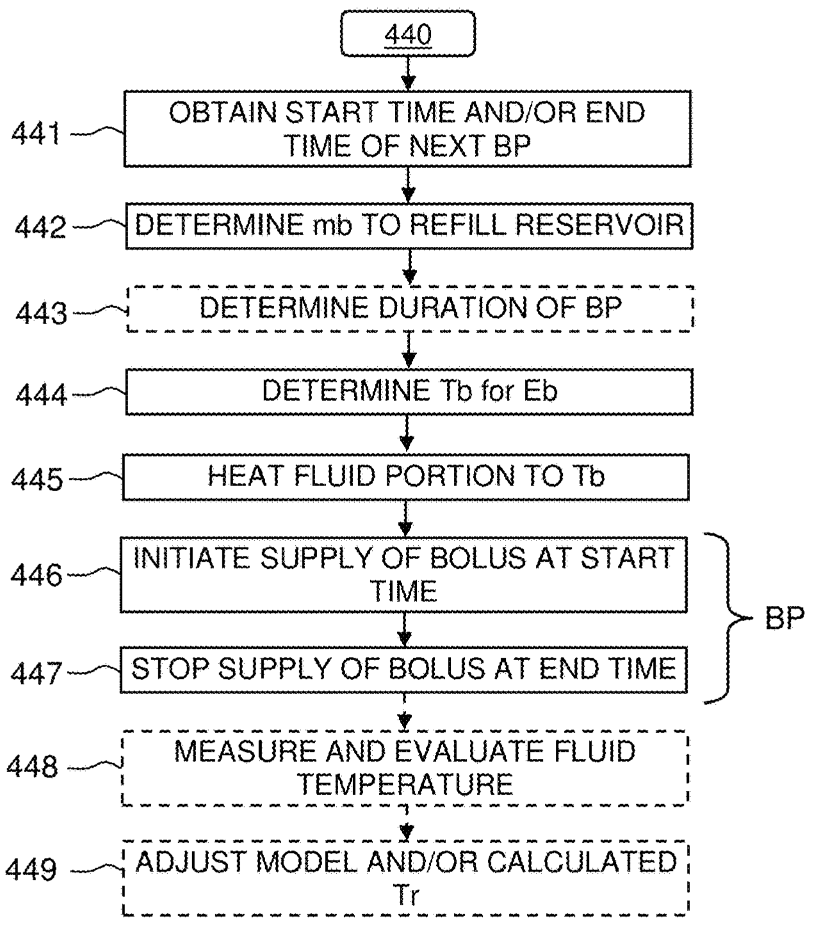

FIG. 4F is a flow chart of a procedure 440 that may be performed as part of steps 204-205 in the method 200 of FIG. 2A. The procedure 440 will be described with reference to FIGS. 3A-3C. In step 441, the start time and/or the end time of the next bolus period, BP, is obtained. This corresponds to obtaining ts and/or the in FIGS. 3A-3C. In step 442, the bolus mass (mb) is determined to refill the reservoir 50. Assuming that the fluid removal rate (qc(t)) is known, the total fluid removal for the fluid supply cycle is given by the fluid removal rate and the duration of the fluid supply cycle. If the bolus supply rate is fixed, the procedure 440 may comprise a step 443 of determining the required duration of the bolus period to supply mb. Based on the required duration, the start time and/or the end time of the BP may be determined in step 443. It is realized that step 443 is optional and that the duration of the BP may be fixed and given by start and end times obtained in step 441. In step 444, the bolus temperature (Tb) is determined, for example as described with reference to FIGS. 4A-4E. Steps 441-444 are completed at least Δt1 before ts. In step 445, the supply sub-system 4 is operated to heat a fluid portion to Tb. In step 446, at time ts, BP is started by initiating the supply of the bolus. In step 447, at time the, BP is terminated by stopping the supply of the bolus.

As shown by dashed lines, the procedure 440 may comprise an optional step 448 of obtaining, at a selected time point, a measured value indicative of the momentary fluid temperature in the reservoir. Step 448 may be performed at any time during a fluid supply cycle and need not be performed for each fluid supply cycle. The measured value may be obtained in correspondence with the measured value 425 (FIG. 4D). In step 448, the measured value is evaluated in relation to a calculated value of Tr for the selected time point. If a significant deviation is detected in step 448, step 449 is performed to adjust the calculated value of Tr and/or the calculation model 400 based on the measured value. For example, the calculated value may be adjusted by applying the measured value 426 as a reference value for subsequent calculation of Tr(t), similar to the measured value 425 (Tr(t0)). The calculation model 400 may be adjusted by modifying one or more parameters of the calculation model 400 so as to match the calculated value to the measured value at the selected time point.

In some embodiments, the control device 7 is configured to cause the supply sub-system 4 to supply the bolus when the reservoir 50 has a predefined weight as measured by the scale 52 (FIGS. 1A-1B). This means that the start of the BP is dynamic and triggered by the weight signal S2. Reverting to step 441 in FIG. 4F, the start time ts of the BP may be estimated based on mr(t), be it calculated in accordance with FIGS. 4D-4E or measured by the scale 52. In the example of FIG. 3A, assuming that BP is triggered when mr is m1, step 441 may determine ts by extrapolating the curve 301 from any time point during the IP.

Figure 5A:
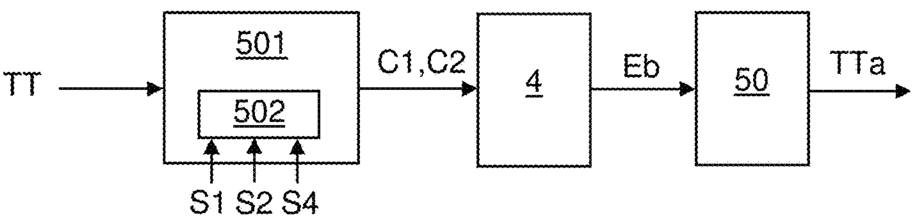
FIGS. 5A-5B are block diagrams of control structures with open-loop control and closed-loop control, respectively.

In some embodiments, the control device 7 is configured to perform open-loop control of the supply sub-system 4 to achieve the target temperature in the reservoir 50. Such embodiments may be applied when there is no temperature sensor associated with the reservoir 50. Open-loop control enables a simple and robust control of the fluid temperature in the reservoir 50. FIG. 5A is a block diagram of an example control module 501 which is configured to generate control signals C1, C2 for the supply sub-system 4 based on the target temperature, TT. The control module 501 comprises a calculation module 502, which is configured to determine the required energy content of the bolus, Eb, as a basis for the generation of C1, C2. In the illustrated example, the calculation module 502 operates on S1, S2 and S4 (FIG. 1A) to determine Eb. The control signals C1, C2 are provided to the heater 42 and the pumping device 44 in the supply sub-system 4 to generate a bolus with the required energy content, causing the fluid in the reservoir 50 to attain TTa, which is presumed to be substantially equal to TT.

Figure 5B:
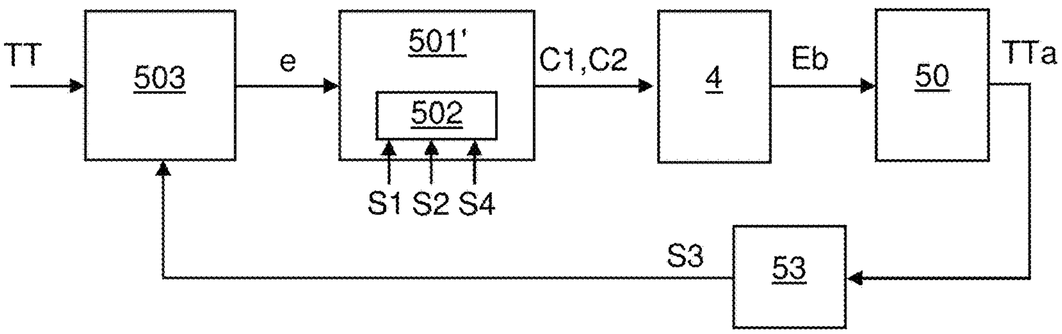

In some embodiments, the control device 7 is configured to perform closed-loop control of supply sub-system 4 to achieve the target temperature in the reservoir 50. Such embodiments may be applied when the dialysis system 1 comprises a temperature sensor that provides a signal indicative of the fluid temperature in the reservoir 50, for example the temperature sensor 53 in FIGS. 1A-1B. Closed-loop control enables accurate control of the fluid temperature in the reservoir 50. FIG. 5B is a block diagram of an example control module 501' which is configured to generate control signals C1, C2 for the supply sub-system 4 based on an error signal e provided by a difference module 503. The control module 501' includes a calculation module 502, which may be identical to the module 502 in FIG. 5A. Like in FIG. 5A, control signals C1, C2 are generated by the control module 501' and provided to the heater 42 and the pumping device 44 in the supply sub-system 4 to generate a bolus with the required energy content Eb, causing the fluid in the reservoir 50 to attain an actual temperature TTa. The actual temperature TTa is measured by the temperature sensor 53 and provided as signal S3 to the difference module 503, which is configured to generate the error signal e to represent the difference between TT and TTa. The control module 501' comprises any conventional control algorithm, such as a P, PI, or PID algorithm, for generating the control signals C1, C2 based on the error signal e. In some embodiments, the control arrangement in FIG. 5B is operated to modify C1, C2 during an on-going BP. However, it is realized the response time may be significant between a change in C1, C2 and a change in TTa as measured by sensor 53. Thus, in some embodiments, the control arrangement in FIG. 5B is operated to modify C1, C2 before but not during the respective bolus period BP.

Figure 6A:
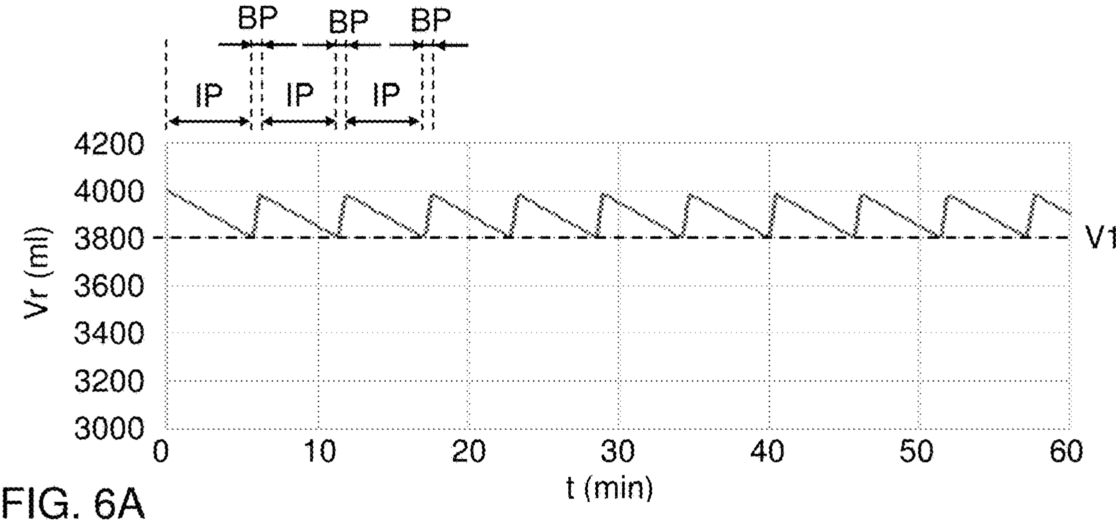
FIGS. 6A-6B are graphs of fluid volume and fluid temperature as a function of time in a reservoir during intermittent supply of a relatively small bolus.
Figure 6B:
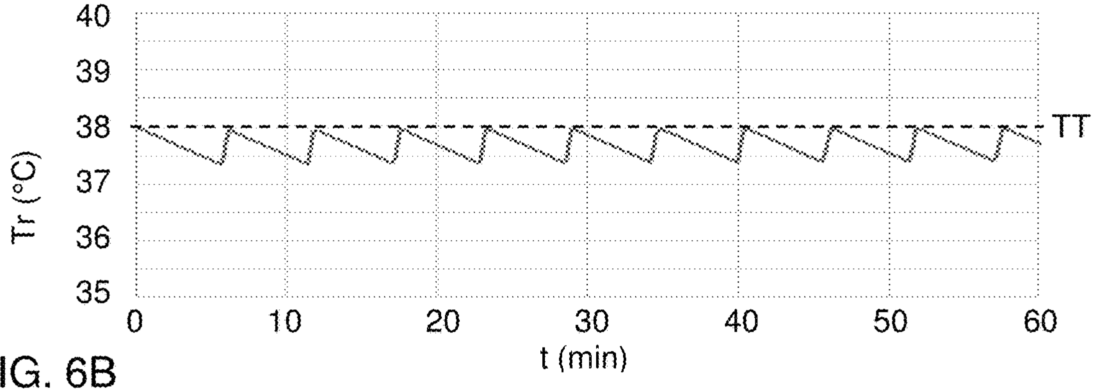
Figures 6C, 6D, 7A, 7B:
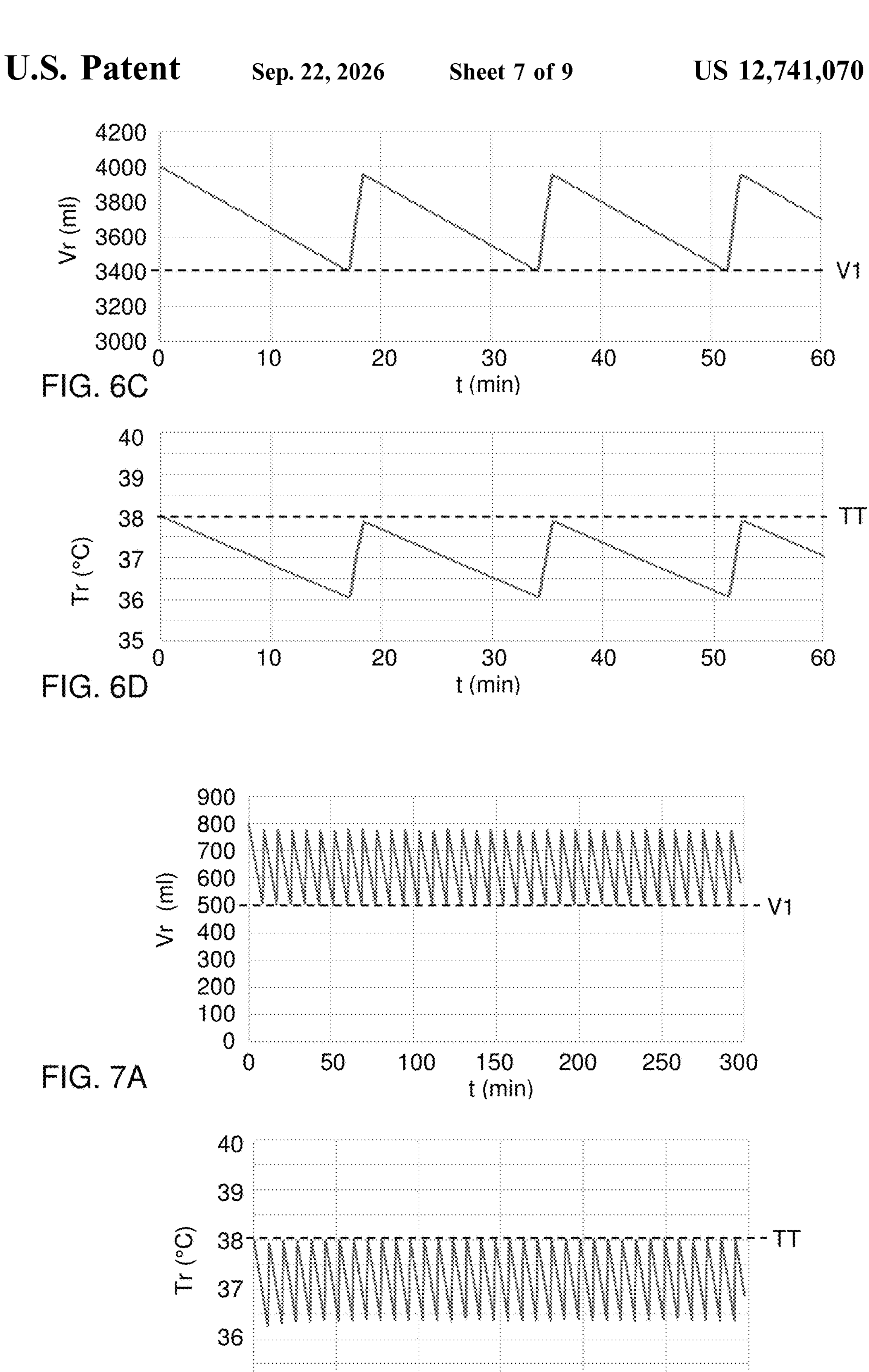
FIGS. 6C-6D are graphs of fluid volume and fluid temperature as a function of time in a reservoir during intermittent supply of a relatively large bolus.
FIGS. 7A-7B are graphs of fluid volume and fluid temperature as a function of time in a reservoir containing a small minimum volume during intermittent bolus supply.

The fluid supply cycles are defined by control parameters, which may be set in dependence of requirements of the treatment sub-system as well as other considerations as described in the following. Two such control parameters are the bolus mass (mb) and the frequency of bolus periods ("BP frequency"), which are interdependent. In some embodiments, as described above, the bolus mass may be set to match the total fluid removal, so that the mass (or volume)

of fluid is kept relatively constant in the reservoir. The bolus mass defines the temperature variation in the reservoir. FIGS. 6A and 6C are graphs of fluid volume (Vr) in the reservoir as a function of time for a bolus volume of 200 ml and 600 ml, respectively. FIGS. 6B and 6D are corresponding graphs of fluid temperature (Tr) in the reservoir with a target temperature (TT) of 38° C. As seen, the temperature variation during a fluid supply cycle is about 0.6° C. and 1.8° C., respectively. If limiting the Tr variation is the only objective, a small bolus mass should be supplied at high frequency. However, such an approach may increase cost and complexity of the sub-systems 3, 4, which have to be designed for frequent preparation and supply of a bolus mass with the correct composition and temperature. For example, if the treatment fluid is generated by mixing water and concentrate(s), the TF sub-system 3 may need to be configured to perform continuous mixing and send treatment fluid to the drain between bolus periods. This results in waste of treatment fluid and is costly. Further, the ultrafiltration accuracy may suffer if the measurement of fluid mass in the reservoir 50 by scale 52 is interrupted by frequent bolus periods. Therefore, a balance between temperature swing and BP frequency is sought. It is presently believed that a temperature swing of less than approximately 5° C. is acceptable. Even better performance is achieved for a temperature swing of less than approximately 4° C., 3° C., 2° C. or 1° C. This allowable temperature swing may be used as a design parameter for the fluid supply cycles, to determine the bolus mass and thus the BP frequency. Further, it is presently believed that a lower limit of the time between bolus periods is 5 minutes, and preferably 10 or 15 minutes. An upper limit may be 30 minutes, 1 hour or 2 hours. Ultimately, the upper limit is given by the fluid removal rate at the reservoir (qc in Appendix A) and the size of the reservoir. For example, treatment fluid is typically, depending on patient size, consumed at a rate of 20-100 ml/min during extracorporeal blood therapy.

Another control parameter of the fluid supply cycles is the minimum fluid mass (volume) in the reservoir. The minimum fluid mass is attained at the end of the idle period (IP), represented as V1 in FIGS. 6A and 6C, and may be considered a buffer volume. The buffer volume enables continued dialysis therapy even if the TF sub-system 3 or the supply sub-system 4 is temporarily disabled, for example during replacement of an empty bag of treatment fluid or concentrate. This would suggest a large buffer volume in the reservoir, for example at least about 50%, 60%, 70%, 80% or 90% of its maximum fluid volume. However, a large buffer volume also results a large surface area A for energy loss to the environment (cf. Appendix A) and thereby increases the required bolus energy. If the bolus mass is set to match the total fluid removal, an increased bolus energy corresponds to an increased bolus temperature (Tb). In some scenarios, Tb may need to be as high as 70° C. As noted above, such fluid temperatures are not tenable for all treatment fluids. Moreover, patient safety may be compromised as an error may lead to hot fluid being supplied to the treatment sub-system 6. It is presently believed that the buffer volume should be kept small, yet large enough to sustain dialysis therapy if the supply of fluid to the reservoir is temporarily interrupted. Thus, the buffer volume may be set in dependence of the removal rate of fluid from the reservoir during on-going therapy.

FIG. 7A is a graph of fluid volume (Vr) in the reservoir as a function of time for a buffer volume of 500 ml. FIG. 7B is a corresponding graph of fluid temperature (Tr) in the reservoir for a target temperature of 38° C. Assuming that treatment fluid is removed from the reservoir at a rate of 35 ml/min, the result in FIGS. 7A-7B is achieved with a bolus temperature (Tb) of 41° C. It is presently believed that the buffer volume, in view of normal consumption rates of treatment fluid during dialysis therapy, should be in the range of 300-2000 ml, 300-1500 ml or 300-1000 ml. The approach of using a relatively small buffer volume also ensures patient safety should the calculation model be slightly inaccurate. For example, if the calculation model calculates the bolus temperature with an error of ±1° C., the system stabilizes with relatively small temperature error in relation to the target temperature, TT. This is shown in FIGS. 7C-7D, where the bolus temperature is 40° C. and 42° C., respectively.

There are many conceivable variations and extensions of the technique described in the foregoing. A few will be described in the following.

In some embodiments, a temperature sensor is arranged in direct contact with the reservoir 50 (cf. 53 in FIGS. 1A-1B), preferably with insulation towards the environment, to measure the actual fluid temperature in the reservoir. This may allow closed-loop control and mitigate errors in energy loss as determined by the calculation model.

In some embodiments, the fluid temperature in the reservoir 50 is measured intermittently, for example every 30 minutes, by sending a dose of fluid from the reservoir to a downstream temperature sensor, for example in the treatment sub-system 6. In one implementation, the treatment sub-system 6 comprises a conductivity sensor that includes a temperature sensor that may be used for measuring the temperature of the dose of fluid.

In some embodiments, blood temperature is measured by a temperature sensor in contact with the blood downstream of the dialyzer 10, and the fluid temperature in the reservoir 50 is estimated based on the measured blood temperature.

In some embodiments, the temperature sensor (80 in FIG. 1A) for measuring ambient temperature may be omitted, for example if the ambient temperature is well-controlled at the location of the dialysis system 1.

In some embodiments, the reservoir is provided with insulation material, for example in the reservoir wall, by encasing the reservoir in an insulated cabinet, or by attaching a multi-use insulating sleeve. The provision of insulation will allow for lower bolus temperature and thus improve patient safety.

The technique presented herein allows for manual control of the fluid temperature in the reservoir 50. A physician may choose to warm or cool the patient, depending on the patient's condition. For example, cooling may help avoid hemodynamic instability. Thus, a manual feedback loop is possible, where the physician measures the patient body temperature, makes a decision if warming or cooling is the best therapy option, and then adjusts the target temperature. This way, static errors created by the calculation model may be overruled.

In some embodiments, the reservoir 50 is intermittently emptied completely of treatment fluid. For example, all fluid may be removed from the reservoir at regular intervals, for example every 24 hours, to mitigate the risk of precipitation and/or microbial growth. A complete emptying of the reservoir enables the reservoir to be refilled with fluid at a known temperature, thereby resetting the estimation of the fluid temperature in the reservoir. The emptying may be done gradually by allowing the fluid to be consumed by the dialysis therapy, or by dumping the remaining fluid in the reservoir to drain. A complete emptying of the reservoir 50 may be detected based on signal S2 from scale 52 (FIGS. 1A-1B).

In some embodiments, gas may be released from the fluid inside the reservoir. For example, as noted above, carbon dioxide may be released from treatment fluid as its temperature is increased. The gas may be removed from the reservoir in any known way. In some embodiments, the gas is removed by the complete emptying of the reservoir, for example by continuing the emptying process for a time period after detecting that all treatment fluid has been removed from the reservoir.

The temperature in the reservoir may not be homogenous. Inhomogeneities may be caused by warm fluid rising to the top of the reservoir and cooler fluid accumulating at the bottom. Further, if the bolus is introduced at the top of the reservoir, and fluid is drawn from the bottom, there is an increased risk of a temperature gradient forming in the reservoir. A few ways of mitigating this effect are described in the following.

In some embodiments, the bolus is introduced at an entry point at the bottom of the reservoir 50, and fluid is drawn from an exit point at the bottom of the reservoir 50, with the locations of the entry and exit points being separated and arranged to promote mixing. In some embodiments, the bolus flow rate is set to cause movement, and thus mixing, within the fluid in the reservoir 50. In some embodiments, the reservoir 50 comprises an entry nozzle for the bolus with a size and/or shape to promote mixing in the reservoir 50. In some embodiments, a small buffer volume is retained in the reservoir 50 to avoid formation of a large stagnant fluid volume within the reservoir 50. The buffer volume may be set as discussed in relation to FIGS. 7A-7D.

The dialysis therapy may be temporarily stopped, for example as a result of various alarm conditions detected by the control device 7, by actions required for the care of the patient, or for management actions such as a change of fluid. In some implementations, the control device 7 may cause the treatment sub-system 6 to stop the removal of fluid from the reservoir 50 to conserve treatment fluid. However, the fluid temperature would fall during such a stop. In some embodiments, the control device 7 is instead configured to operate the treatment sub-system 6 to remove fluid from the reservoir 50 and operate the supply sub-system 4 to perform the fluid supply cycles also when dialysis therapy is temporarily stopped. This enables the temperature in the reservoir to be maintained at the target temperature and will facilitate restart of therapy. In an alternative embodiment, to save treatment fluid, the control device 7 is configured to calculate the temperature drop in the reservoir 50 during the stop of therapy, and then operate the supply sub-system 4 with elevated bolus temperature to increase the fluid temperature in the reservoir 50 as fast as possible when therapy is resumed. In a further embodiment, the control device 7 is configured to cause the reservoir 50 to be completely emptied of fluid if the fluid temperature (measured or estimated) in the reservoir 50 has fallen below a minimum limit, and operate the supply sub-system 4 to refill the reservoir 50 with fluid at a desired temperature. The minimum limit may be set to represent a fluid temperature that cannot be increased to the target temperature within reasonable time.

The technique of controlling the fluid temperature in a non-heated reservoir is not only applicable to treatment fluid. In some embodiments, the reservoir may instead contain water for use in dialysis therapy. An example of such a dialysis system 1 is shown in FIG. 8A. The following description will focus on differences compared to the dialysis system in FIG. 1A. The dialysis system 1 in FIG. 8A comprises a TF sub-system 3, a supply sub-system 4, a storage sub-system 5, and a treatment sub-system 6, but differs from the dialysis system 1 in FIG. 1A by the supply-sub-system 4 and the TF sub-system 3. Specifically, the supply sub-system 4 is configured to supply purified water for use in the dialysis system 1. The supply sub-system 4 may or may not comprise a device for purifying incoming water. Like in FIG. 1A, the supply sub-system 4 is operable to heat the fluid (purified water) by a heater 42 and to supply, by a pumping device 44, a bolus of heated fluid on path 4' to the reservoir 50 in the storage sub-system 5. The treatment sub-system 6 is operable to obtain purified water from the reservoir 50 on path 5'. The TF sub-system 3 is included in the treatment sub-system 6 and comprises a mixing arrangement for preparing treatment fluid (TF) by mixing the purified water with one or more concentrates. The flow control arrangement 60 is configured to obtain the TF from the TF sub-system 3 on path 3' and distribute the TF in accordance with the RRT that is performed by the treatment sub-system 6.

Although not shown in FIG. 8A, the dialysis system 1 is operated by a control device, which may be configured in correspondence with the control device 7 in FIG. 1A. The control device 7 is thereby configured to control the temperature of the water in the reservoir 50 to a target temperature. The target temperature may be set to achieve a designated temperature of the resulting treatment fluid.

Figure 8B:
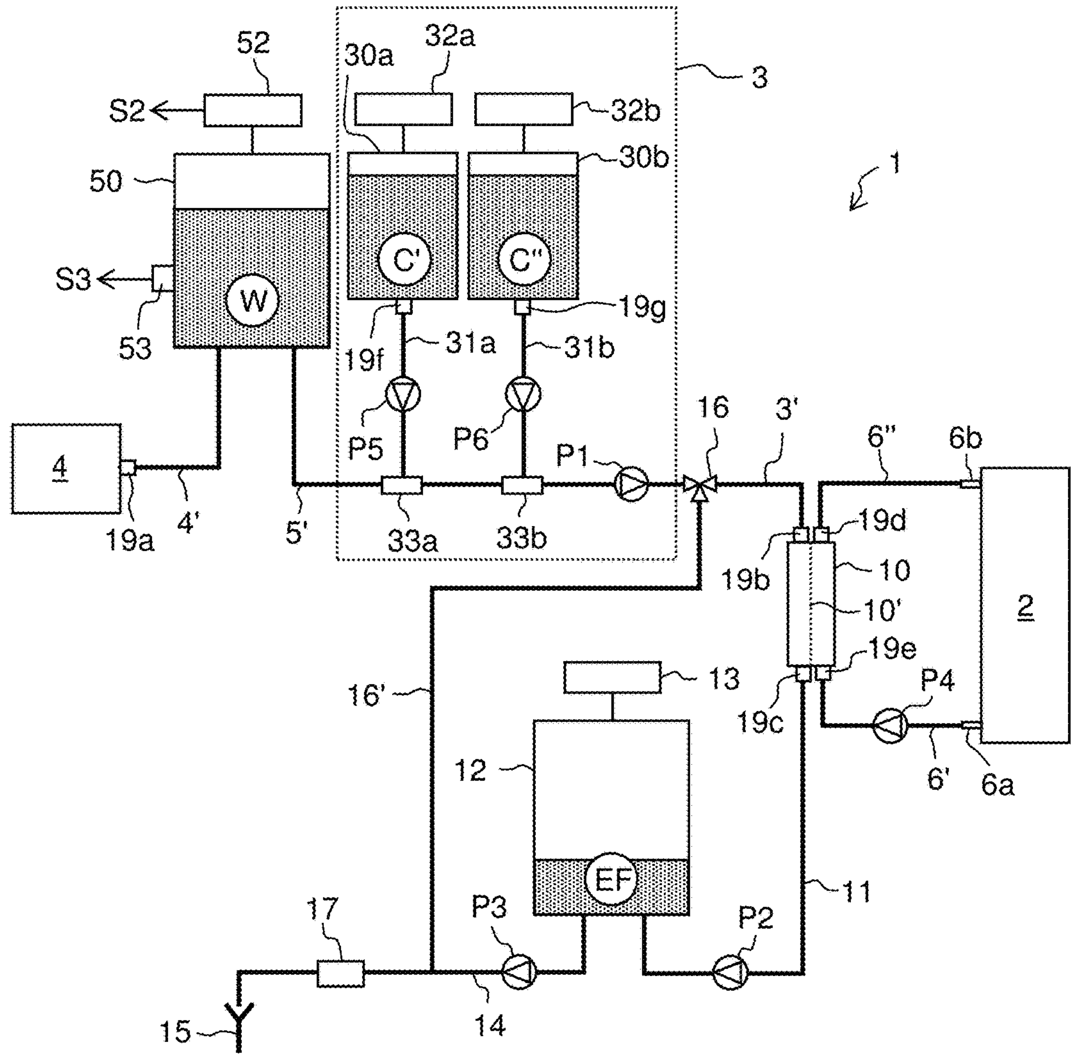
FIG. 8B shows an implementation of the dialysis system in FIG. 8A for hemodialysis by CRRT.

FIG. 8B shows an adaptation of the dialysis system 1 in FIG. 1B in accordance with FIG. 8A. The reservoir 50 holds purified water, represented by W. In the illustrated example, the TF sub-system 3 is configured to generate treatment fluid by mixing water with two liquid concentrates C', C" held in a respective container 30*a*, 30*b*. Fluid paths 31*a*, 31*b* extend from containers 30*a*, 30*b* to junctions 33*a*, 33*b* on path 5'. The dialysis system 1 further comprises a pumping arrangement with a pump P5 in fluid path 31*a*, a pump P6 in fluid path 32*b*, and a pump P1 in path 5' downstream of junctions 33*a*, 33*b*. The pump P1 is arranged in path 5' to define the flow rate of treatment fluid, and pumps P5, P6 are arranged in fluid paths 31*a*, 31*b* to define the flow of C', C", respectively. Thus, the pumps P5, P6 are operable to control the amounts of C', C" that are mixed with water within path 5'. In the illustrated example, the dialysis system 1 further comprises a bypass path 16', which is fluidly connected to path 5' by a valve arrangement 16. The bypass path 16' extends to the drain path 14, upstream of a conductivity sensor 17. The dialysis system 1 may be operated in a calibration phase and a treatment phase. In the calibration phase, the valve arrangement 16 is operated to direct fluid from path 5' into bypass path 16', and pumps P1, P5 and P6 are operated to generate different mixtures of W, C' and C" in path 5'. These mixtures are directed into the bypass path 16' and through the conductivity sensor 17. When the conductivity of the respective mixture matches a predefined value, a relation between the speeds of the pumps P1, P5, P6 is obtained for use as calibration data in the treatment phase. In the treatment phase, the valve arrangement 16 is operated to direct fluid along path 5' into the dialyzer 10, while pumps P1, P5 and P6 are operated in accordance with the calibration data to generate the treatment fluid with a designated composition. In the example shown in FIG. 8B, the disposable arrangement discussed in relation to FIG. 1B also includes fluid lines 31*a*, 31*b*, which are releasably connected by connectors 19*f*, 19*g* to the containers 30*a*, 30*b*. The conductivity sensor 17 may or may not be included in the disposable arrangement.

It is realized that the concentrates C', C" may be at room temperature when mixed with the water from the reservoir 50, thereby reducing the temperature of the resulting treatment fluid in relation to the water in the reservoir 50. In some embodiments, the control device 7 is configured to account for this cooling effect when setting the target temperature of the water in the reservoir 50.

While the subject of the present disclosure has been described in connection with what is presently considered to be the most practical embodiments, it is to be understood that the subject of the present disclosure is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results.

APPENDIX A

Heat loss may be described by $Q_h=h*A*\Delta T$, where $Q_h$ is heat dissipation per unit time [W], h is a heat transfer constant, A is surface area [$m^2$] and $\Delta T$ is the temperature difference [° C.] to the ambient temperature, $T_a$. As $\Delta T$ and A may change over time, the equation is generalized as:

$$Q_h(t) = h * A(t) * (T(t) - T_a(t)) \tag{1}$$

In a reservoir with fixed surface area and containing a fluid of mass $m_r$, and assuming a fixed ambient temperature, the temperature in the reservoir will decrease exponentially according to:

$$T_r(t) = T_a + (T_0 - T_a)\cdot e^{-\frac{h\cdot A(t)}{c\cdot m_r(t)}t} \tag{2}$$

with c being the specific heat capacity of the fluid, and $T_0$ being a temperature at a reference time point $t_0$.

The heat dissipation $Q_h(t)$ at any time may be calculated using Eq. 1 and Eq. 2, and may be integrated over time to calculate the total energy loss by dissipation $E_h$:

$$E_h(t) = \int_0^t Q_h(t)dt = \int_0^t \left(h\cdot A(t)\cdot (T_0 - T_a)\cdot e^{-\frac{h\cdot A}{c\cdot m_r(t)}t}\right)dt \tag{3}$$

Assuming that fluid is removed from the reservoir at a mass flow rate of $q_c$, the mass in the reservoir will change with time:

$$m_r(t) = m_r(t_0) - q_c\cdot t \tag{4}$$

where $t_0$ is the reference time point. Here, it is assumed that the fluid removal rate is constant, but it may alternatively be a function of time, $q_c(t)$.

In one example, the heat dissipating area during the idle period is modeled under the assumption that the reservoir is spherical, for example if the reservoir is bag made of pliable material. For a sphere, the surface area is a function of fluid volume in the reservoir, V(t):

$$A_{IP}(t) = k_1\cdot V(t)^{\frac{2}{3}} = k_1\cdot\left(\frac{m_r(t)}{\rho}\right)^{\frac{2}{3}} = k_2\cdot (m_r(t_0) - q_c\cdot t)^{\frac{2}{3}} \tag{5}$$

where ρ is the density of the fluid.

More advanced models of A(t) or h·A(t) as a function of $m_r(t)$ are conceivable, for example based on empirical data for a specific type of reservoir.

The instantaneous energy loss from the reservoir via the fluid removal may be calculated as:

$$Q_d(t) = c\cdot q_c\cdot (T_r(t) - T_a) = c\cdot q_c\cdot (T_0 - T_a)\cdot e^{-\frac{h\cdot A_{IP}(t)}{c\cdot m_r(t)}t} \tag{6}$$

In this calculation, the thermal energy content of the fluid is calculated as additional energy relative to ambient temperature. In a variant, the thermal energy content may instead be calculated in absolute temperature [° K].

Based on Eq. 6 and Eq. 3, the total energy loss during an idle period (IP) extending from t=0 to t=ts is given as:

$$E_{lossIP} = \int_0^{ts}\left((h\cdot A_{IP}(t) + c\cdot q_c)\cdot (T_0 - T_a)\cdot e^{-\frac{h\cdot A_{IP}(t)}{c\cdot m_r(t)}t}\right)dt \tag{7}$$

The fluid removal may continue or be stopped during the bolus period (BP), depending on system design. In the following, the removal is assumed to continue at the same flow rate, $q_c$. The mass in the reservoir during the bolus period (ts<t<te) is:

$$m_r(t) = m_r(t_0) - q_c\cdot t + q_b\cdot (t - ts) \tag{8}$$

with $q_b$ being the mass flow rate of the bolus, which is also assumed to be constant during the bolus period. The heat dissipating area during the bolus period will follow from Eq. 5 and Eq. 8:

$$A_{BP}(t) = k_1\cdot V(t)^{\frac{2}{3}} = k_1\cdot\left(\frac{m_r(t)}{\rho}\right)^{\frac{2}{3}} = k_2\cdot (m_r(t_0) - q_c\cdot t + q_b\cdot (t - ts))^{\frac{2}{3}} \tag{9}$$

The temperature in the reservoir will change as a function of the mass and energy provided by the bolus, in combination with the energy that is lost via dissipation and fluid removal. During the bolus period (ts<t<te), power and energy added to the reservoir by the bolus flow, $q_b$, are given by:

$$Q_b(t) = c\cdot q_b\cdot (T_b - T_a) \tag{10}$$

$$E_b(t) = \int_{ts}^t Q_b(t)dt = \int_{ts}^t (c\cdot q_b\cdot (T_b - T_a))dt \tag{11}$$

The temperature of the fluid in the reservoir increases during the bolus period due to energy supplied by bolus. Assuming complete mixing, and for the moment ignoring the energy loss during the bolus period, the energy content of the fluid in the reservoir is given by:

$$E_r(t) = E_r(ts) + E_b(t) = c \cdot m_r(t) \cdot (T_r(t) - T_a) \tag{12}$$

with $E_r$(ts) being the energy content of the reservoir at the start of the bolus period:

$$E_r(ts) = c \cdot m_r(ts) \cdot (T_r(ts) - T_a) \tag{13}$$

The combination of Eq. 11, Eq. 12 and Eq. 13 yields an equation for the temperature of the fluid in the reservoir:

$$T_r(t) = T_a + \frac{c \cdot m_r(ts) \cdot (T_r(ts) - T_a) + \int_{ts}^{t} (c \cdot q_b \cdot (T_b - T_a))dt}{c \cdot (m_r(t_0) - q_c \cdot t + q_b \cdot (t - ts))} \tag{14}$$

Eq. 14 describes how the temperature increases in the reservoir due to the bolus during the bolus period, if the energy loss during the bolus period is ignored.

The energy loss during the bolus period is given by both energy loss by dissipation, according to Eq. 3, and energy loss by fluid removal, according to Eq. 6. These losses are in turn dependent on the temperature of the fluid in the reservoir. It is thus more complicated to analytically calculate the energy loss during the bolus period. However, an equation for calculating T (t) in view of energy loss during the bolus period may be derived, if not analytically then by empiric estimation. Assuming that an equation for T (t) is available, the energy loss during the bolus period is given by:

$$E_{lossBP} = \int_{ts}^{te} (Q_h(t) + Q_d(t))dt == \int_{ts}^{te} (h \cdot A_{BP}(t) \cdot (T_r(t) - T_a) + c \cdot q_c \cdot (T_r(t) - T_a))dt == \int_{ts}^{te} ((h \cdot A_{BP}(t) + c \cdot q_c) \cdot (T_r(t) - T_a))dt \tag{15}$$

Finally, the total energy loss during a full fluid cycle comprising an idle period and a bolus period is given by:

$$E_{lossTOT} = E_{lossIP} + E_{lossBP} = \int_{0}^{ts} \left( (h \cdot A_{IP}(t) + c \cdot q_c) \cdot (T_0 - T_a) \cdot e^{-\frac{h \cdot A_{IP}(t)}{c \cdot m_r(t)} t} \right) dt + + \int_{ts}^{te} ((h \cdot A_{BP}(t) + c \cdot q_c) \cdot (T_r(t) - T_a))dt \tag{16}$$

The invention claimed is:

1. A dialysis system comprising:

a supply sub-system configured to supply a fluid and comprising a heating device for heating the fluid, a storage sub-system comprising a non-heated reservoir, wherein the non-heated reservoir is fluidly connected to receive the fluid from the supply sub-system and configured to hold an intermediate supply of the fluid during operation of the dialysis system, a treatment sub-system configured to obtain the fluid from the storage sub-system and perform a dialysis treatment by use of the fluid, and a control device configured to operate the treatment sub-system to perform the dialysis treatment, wherein the control device is further configured to operate the supply sub-system to perform a sequence of fluid supply cycles causing a sequence of time-separated boluses of the fluid to be supplied to the non-heated reservoir, wherein a respective fluid supply cycle among the fluid supply cycles is assigned a target temperature and comprises a predefined number of boluses, wherein the supply sub-system is operated to achieve, through the predefined number of boluses, the target temperature of the fluid in the non-heated reservoir for the respective fluid supply cycle.

2. The dialysis system of claim 1, wherein the target temperature is a temperature of the fluid in the non-heated reservoir at a target time point within the respective fluid supply cycle, or a time-average of the temperature of the fluid in the non-heated reservoir during the respective fluid supply cycle.

3. The dialysis system of claim 1, wherein the control device is configured to: obtain the target temperature, determine an energy content of the predefined number of boluses to attain the target temperature, and operate the supply sub-system to prepare, in accordance with the energy content, a fluid portion for use in generating the predefined number of boluses.

4. The dialysis system of claim 3, wherein the control device is configured to: determine a designated size of a respective bolus among the predefined number of boluses, and a designated temperature of the respective bolus that result in the predefined number of boluses having the energy content, operate the supply sub-system to heat the fluid portion to the designated temperature by use of the heating device, and operate the supply sub-system to generate the respective bolus with the designated size from the fluid portion that has the designated temperature.

5. The dialysis system of claim 4, wherein the control device is configured to: determine an amount of the fluid that is removed from the non-heated reservoir by the treatment sub-system during the respective fluid supply cycle, and determine the energy content of the predefined number of boluses partly based on the amount of the fluid that is removed from the non-heated reservoir.

6. The dialysis system of claim 5, wherein the control device is configured to determine the designated size of the respective bolus based on the amount of the fluid that is removed from the non-heated reservoir during the respective fluid supply cycle.

7. The dialysis system of claim 6, wherein the control device is configured to, based on the designated size of the respective bolus, determine the designated temperature of the respective bolus to achieve the energy content of the predefined number of boluses.

8. The dialysis system of claim 3, wherein the control device comprises a calculation model, which is configured to: estimate a total energy loss from the fluid in the non-heated reservoir during the respective fluid supply cycle, and determine the energy content of the predefined number of boluses based on the total energy loss during the respective fluid supply cycle.

9. The dialysis system of claim 8, wherein the total energy loss comprises a first loss portion that represents dissipated thermal energy from the fluid in the non-heated reservoir, and a second loss portion that represents energy loss by removal of the fluid from the non-heated reservoir by the treatment sub-system.

10. The dialysis system of claim 9, wherein the total energy loss further comprises a third loss portion that represents dissipated thermal energy from the fluid in a flow path, which extends from the supply sub-system to the non-heated reservoir.

11. The dialysis system of claim 8, wherein the control device is operable in a steady-state mode, in which the target temperature is identical for a plurality of consecutive fluid supply cycles, wherein the control device is configured, in the steady-state mode, to set the energy content of the predefined number of boluses equal to the total energy loss during the respective fluid supply cycle.

12. The dialysis system of claim 8, wherein the calculation model is configured to: calculate a momentary temperature of the fluid in the non-heated reservoir during the respective fluid supply cycle, and operate on the momentary temperature to determine the energy content of the predefined number of boluses so as to achieve the target temperature.

13. The dialysis system of claim 12, wherein the control device is configured to obtain a measured value, which is indicative of the momentary temperature of the fluid in the non-heated reservoir at a reference time point, wherein the calculation model-is configured to calculate the momentary temperature of the fluid in the non-heated reservoir based on the measured value.

14. The dialysis system of claim 13, wherein the control device is configured to: obtain a further measured value, which is indicative of the momentary temperature of the fluid in the non-heated reservoir at a time point subsequent to the reference time point, and adjust a calculated momentary temperature at the time point and/or the calculation model based on the further measured value.

15. The dialysis system of claim 12, wherein the calculation model is further configured to: calculate a momentary heat dissipating area of the non-heated reservoir and/or a momentary amount of the fluid in the non-heated reservoir; and estimate the momentary temperature as a function of the momentary heat dissipating area and/or the momentary amount of the fluid in the non-heated reservoir.

16. The dialysis system of claim 8, wherein the control device is configured to obtain input data for use by the calculation model, the input data being indicative of a duration of the respective fluid supply cycle, a timing of the respective bolus within the respective fluid supply cycle, a duration of the respective bolus, and a time profile for removal of the fluid from the non-heated reservoir during the respective fluid supply cycle.

17. The dialysis system of claim 16, wherein the control device is configured to determine the time profile based on an operational setting of the treatment sub-system or a measured flow rate of the fluid into the treatment sub-system.

18. The dialysis system of claim 8, wherein the respective bolus is supplied to the non-heated reservoir during a bolus period, wherein the calculation model comprises a function for estimating energy loss from the non-heated reservoir during the bolus period, the function accounting for change in energy loss caused by temperature change of the fluid in the non-heated reservoir as a result of the supply of the respective bolus.

19. The dialysis system of claim 3, which further comprises an ambient sensor, which is arranged to measure an ambient temperature at the storage sub-system, and the control device is configured to determine the energy content of the predefined number of boluses based on the ambient temperature.

20. The dialysis system of claim 1, wherein the control device is configured to operate the supply sub-system to perform the sequence of fluid supply cycles to impart, between consecutive boluses, a temperature decrease of less than approximately 5° C., 4° C., 3° C., 2° C. or 1° C. to the fluid in the non-heated reservoir.

21. The dialysis system of claim 1, wherein the control device is configured to operate the supply sub-system to perform the respective fluid supply cycle with a duration of more than 5, 10 or 15 minutes and less than 30, 60 or 120 minutes.

22. The dialysis system of claim 1, wherein the non-heated reservoir is a disposable component.

23. The dialysis system of claim 1, wherein the storage sub-system comprises a scale for measuring a weight of the non-heated reservoir, and the control device is configured to cause the supply sub-system to supply the respective bolus when the non-heated reservoir has a predefined weight, as measured by the scale.

24. The dialysis system of claim 1, wherein the control device is configured to perform open-loop control of the supply sub-system to achieve the target temperature.

25. The dialysis system of claim 1, further comprising a measurement arrangement, which is configured to measure, for the fluid in the non-heated reservoir, a temperature value that corresponds to the target temperature, wherein the control device is configured to operate the supply sub-system to adjust, based on a difference between the target temperature and the measured temperature value, a size of the respective bolus and/or a temperature of the fluid that is to be supplied by the respective bolus.

26. The dialysis system of claim 1, wherein the fluid is a treatment fluid for use in the dialysis treatment.

27. The dialysis system of claim 1, wherein the fluid is water, and the treatment sub-system comprises a mixing arrangement which is configured to mix the fluid with one or more concentrates to provide a treatment fluid for use in the dialysis treatment.

28. A computer-implemented method of operating a dialysis system comprising a supply sub-system, a storage sub-system, and a treatment sub-system, the method comprising:

operating the treatment sub-system to obtain a fluid from a non-heated reservoir in the storage sub-system and perform a dialysis treatment by use of the fluid; and operating the supply sub-system to perform a sequence of fluid supply cycles causing a sequence of time-separated boluses of the fluid to be supplied to the non-heated reservoir, wherein a respective fluid supply cycle among the fluid supply cycles is assigned a target temperature and comprises a predefined number of boluses, wherein the supply sub-system is operated to achieve, through the predefined number of boluses, the target temperature of the fluid in the non-heated reservoir for the respective fluid supply cycle.

29. A non-transitory computer-readable medium comprising computer instructions which, when executed by processing circuitry, cause the processing circuitry to perform the method of claim 28.

* * * * *